US 11,432,810 B2

(12) United States Patent
Gregersen et al.

(10) Patent No.: US 11,432,810 B2
(45) Date of Patent: Sep. 6, 2022

(54) SYSTEMS AND METHODS FOR SURGICAL RETRACTION

(71) Applicant: Innovasis, Inc., Salt Lake City, UT (US)

(72) Inventors: Colin Gregersen, Salt Lake City, UT (US); Navid Mahpeykar, Camarillo, CA (US); Jason Glad, Nibley, UT (US)

(73) Assignee: Innovasis, Inc., Salt Lake City, UT (US)

( * ) Notice: Subject to any disclaimer, the term of this patent is extended or adjusted under 35 U.S.C. 154(b) by 129 days.

(21) Appl. No.: 15/930,007

(22) Filed: May 12, 2020

(65) Prior Publication Data

US 2021/0353277 A1 Nov. 18, 2021

(51) Int. Cl.
*A61B 17/02* (2006.01)
*A61B 17/00* (2006.01)
*A61B 90/57* (2016.01)

(52) U.S. Cl.
CPC .. *A61B 17/0206* (2013.01); *A61B 2017/0046* (2013.01); *A61B 2017/0256* (2013.01); *A61B 2090/571* (2016.02)

(58) Field of Classification Search
CPC ............ A61B 17/0206; A61B 17/0218; A61B 17/025; A61B 17/02; A61B 2017/0256; A61B 2017/0262
See application file for complete search history.

(56) References Cited

U.S. PATENT DOCUMENTS

| 3,965,890 | A | * | 6/1976 | Gauthier ............ A61B 17/0293 600/215 |
| 6,224,545 | B1 | | 5/2001 | Cocchia et al. |
| 6,360,750 | B1 | | 3/2002 | Gerber et al. |
| 6,849,064 | B2 | | 2/2005 | Hamada |
| 7,147,599 | B2 | | 12/2006 | Burns et al. |
| 7,207,949 | B2 | | 4/2007 | Miles et al. |
| 7,320,688 | B2 | | 1/2008 | Foley et al. |
| 7,470,236 | B1 | | 12/2008 | Kelleher et al. |
| 7,473,222 | B2 | | 1/2009 | Dewey et al. |
| 7,491,205 | B1 | | 2/2009 | Michelson |
| 7,494,463 | B2 | | 2/2009 | Nehls |
| 7,537,565 | B2 | | 5/2009 | Bass |

(Continued)

FOREIGN PATENT DOCUMENTS

WO WO2017075503 A1 5/2017

*Primary Examiner* — Amy R Sipp
(74) *Attorney, Agent, or Firm* — David Meibos; Maywood IP Law

(57) ABSTRACT

A retractor system may provide access to a surgical site along an access pathway surrounded by tissue. In some embodiments, the retractor system may include three arms and four retractor blades, each having a tissue engagement surface. The second arm may translate along a first retraction direction relative to the first arm. The first retractor blade may be securable to the first arm and the second retractor blade may be securable to the second arm. The third arm may have a connection feature that may be removably securable to a connection interface of the second arm. The third retractor blade may be securable to the third arm and the fourth retractor blade may be securable to a rack between the first and second arms. The third and fourth retractor blades may have cross-sectional shapes oriented generally parallel to the first retraction direction.

22 Claims, 27 Drawing Sheets

(56) References Cited

U.S. PATENT DOCUMENTS

| | | |
|---|---|---|
| 7,556,600 B2 | 7/2009 | Landry et al. |
| 7,582,058 B1 | 9/2009 | Miles et al. |
| 7,625,339 B2 | 12/2009 | Frasier et al. |
| 7,666,189 B2 | 2/2010 | Gerber et al. |
| 7,758,501 B2 | 7/2010 | Frasier et al. |
| 7,785,253 B1 | 8/2010 | Arambula et al. |
| 7,819,801 B2 | 10/2010 | Miles et al. |
| 7,824,410 B2 | 11/2010 | Simonson et al. |
| 7,892,173 B2 | 2/2011 | Miles et al. |
| 7,892,174 B2 | 2/2011 | Hestad et al. |
| 7,905,840 B2 | 3/2011 | Pimenta et al. |
| 7,918,792 B2 | 4/2011 | Drzyzga et al. |
| 7,922,658 B2 | 4/2011 | Cohen et al. |
| 7,935,051 B2 | 5/2011 | Miles et al. |
| 7,935,053 B2 | 5/2011 | Karpowicz et al. |
| 7,946,982 B2 | 5/2011 | Hamada |
| 7,951,154 B2 | 5/2011 | Schwab et al. |
| 7,962,191 B2 | 6/2011 | Marino et al. |
| RE42,525 E | 7/2011 | Simonson |
| 7,985,179 B2 | 7/2011 | Gephart et al. |
| 8,000,782 B2 | 8/2011 | Gharib et al. |
| 8,048,109 B2 | 11/2011 | Garcia-Bengochea |
| 8,062,217 B2 | 11/2011 | Boucher et al. |
| 8,062,218 B2 | 11/2011 | Sebastian et al. |
| 8,105,236 B2 | 1/2012 | Malandain et al. |
| 8,114,016 B2 | 2/2012 | Lo et al. |
| 8,133,173 B2 | 3/2012 | Miles et al. |
| 8,137,284 B2 | 3/2012 | Miles et al. |
| 8,152,720 B2 | 4/2012 | Loftus et al. |
| 8,162,827 B2 | 4/2012 | Abdelgany et al. |
| 8,172,750 B2 | 5/2012 | Miles et al. |
| 8,182,519 B2 | 5/2012 | Loftus et al. |
| 8,187,179 B2 | 5/2012 | Miles et al. |
| 8,192,356 B2 | 6/2012 | Miles et al. |
| 8,192,357 B2 | 6/2012 | Miles et al. |
| 8,192,437 B2 | 6/2012 | Simonson |
| 8,202,216 B2 | 6/2012 | Melkent et al. |
| 8,206,293 B2 | 6/2012 | Reglos et al. |
| 8,211,012 B2 | 7/2012 | Wing et al. |
| 8,226,554 B2 | 7/2012 | McBride et al. |
| 8,262,569 B2 | 9/2012 | Hestad et al. |
| 8,265,744 B2 | 9/2012 | Gharib et al. |
| 8,303,498 B2 | 11/2012 | Miles et al. |
| 8,303,499 B2 | 11/2012 | Hamada |
| 8,303,601 B2 | 11/2012 | Bandeira et al. |
| 8,317,692 B2 | 11/2012 | Loftus et al. |
| 8,353,826 B2 | 1/2013 | Weiman |
| 8,355,780 B2 | 1/2013 | Miles et al. |
| 8,388,527 B2 | 3/2013 | Miles et al. |
| 8,439,832 B2 | 5/2013 | Miles et al. |
| 8,449,463 B2 | 5/2013 | Nunley et al. |
| 8,454,644 B2 | 6/2013 | McDonnell |
| 8,480,576 B2 | 7/2013 | Sandhu |
| 8,500,634 B2 | 8/2013 | Miles et al. |
| 8,512,235 B2 | 8/2013 | Miles et al. |
| 8,517,935 B2 | 8/2013 | Marchek et al. |
| 8,523,768 B2 | 9/2013 | Miles et al. |
| 8,568,306 B2 | 10/2013 | Hardenbrook |
| 8,574,154 B2 | 11/2013 | Loftus et al. |
| 8,591,431 B2 | 11/2013 | Calancie et al. |
| 8,602,982 B2 | 12/2013 | Miles et al. |
| 8,617,062 B2 | 12/2013 | Mire et al. |
| 8,636,656 B2 | 1/2014 | Nichter et al. |
| 8,636,657 B2 | 1/2014 | Hamada |
| 8,663,100 B2 | 3/2014 | Miles et al. |
| 8,672,840 B2 | 3/2014 | Miles et al. |
| 8,679,006 B2 | 3/2014 | Miles et al. |
| 8,696,560 B2 | 4/2014 | Strauss et al. |
| 8,708,899 B2 | 4/2014 | Miles et al. |
| 8,747,307 B2 | 6/2014 | Miles et al. |
| 8,753,270 B2 | 6/2014 | Miles et al. |
| 8,768,450 B2 | 7/2014 | Gharib et al. |
| 8,771,181 B2 | 7/2014 | Garcia-Bengochea |
| 8,801,608 B2 | 8/2014 | Hardenbrook |
| 8,808,172 B2 | 8/2014 | Manzanares |
| 8,821,394 B2 | 9/2014 | Hawkins et al. |
| 8,852,089 B2 | 10/2014 | Blackwell et al. |
| 8,876,687 B2 | 11/2014 | Jones et al. |
| 8,876,851 B1 | 11/2014 | Woolley et al. |
| 8,876,904 B2 | 11/2014 | Pimenta et al. |
| 8,915,846 B2 | 12/2014 | Miles et al. |
| 8,956,283 B2 | 2/2015 | Miles et al. |
| 8,956,285 B2 | 2/2015 | Gephart et al. |
| 8,968,363 B2 | 3/2015 | Weiman et al. |
| 8,977,352 B2 | 3/2015 | Gharib et al. |
| 8,986,344 B2 | 3/2015 | Sandhu |
| 8,992,425 B2 | 3/2015 | Karpowicz et al. |
| 8,998,807 B2 | 4/2015 | Fiorella |
| 9,028,522 B1 | 5/2015 | Prado |
| 9,044,280 B1 | 6/2015 | Arambula et al. |
| 9,055,936 B2 | 6/2015 | Mire et al. |
| 9,060,757 B2 | 6/2015 | Lawson et al. |
| 9,084,591 B2 | 7/2015 | Reglos et al. |
| 9,089,299 B2 | 7/2015 | Nowak et al. |
| 9,131,933 B2 | 9/2015 | Mire et al. |
| 9,179,903 B2 | 11/2015 | Cianfrani et al. |
| 9,192,367 B2 | 11/2015 | Nunley et al. |
| 9,216,016 B2 | 12/2015 | Fiechter et al. |
| 9,220,491 B2 | 12/2015 | Nunley et al. |
| 9,241,619 B2 | 1/2016 | Nowak et al. |
| 9,271,711 B2 | 3/2016 | Hawkins et al. |
| 9,282,957 B2 | 3/2016 | Caner |
| 9,289,248 B2 | 3/2016 | Seex et al. |
| 9,351,718 B1 | 5/2016 | Arambula et al. |
| 9,357,908 B2 | 6/2016 | Frasier et al. |
| 9,357,909 B2 | 6/2016 | Perez-Cruet et al. |
| 9,414,828 B2 | 8/2016 | Abidin et al. |
| 9,486,133 B2 | 11/2016 | Lee et al. |
| 9,486,199 B2 | 11/2016 | Pimenta et al. |
| 9,521,997 B2 | 12/2016 | Hawkins et al. |
| 9,532,774 B2 | 1/2017 | Simonson |
| 9,572,562 B2 | 2/2017 | Miles et al. |
| 9,585,648 B2 | 3/2017 | Heiges et al. |
| 9,615,733 B2 | 4/2017 | Nottmeier |
| 9,615,818 B2 | 4/2017 | Baudouin et al. |
| 9,622,732 B2 | 4/2017 | Martinelli et al. |
| 9,636,097 B2 | 5/2017 | Bass |
| 9,649,101 B2 | 5/2017 | Karpowicz et al. |
| 9,655,505 B1 | 5/2017 | Gharib et al. |
| 9,675,334 B2 | 6/2017 | Heiges et al. |
| 9,681,862 B1 | 6/2017 | Tumialan |
| 9,717,403 B2 | 8/2017 | Kleiner et al. |
| 9,724,137 B2 | 8/2017 | Hynes et al. |
| 9,737,288 B2 | 8/2017 | Karpowicz et al. |
| 9,750,490 B2 | 9/2017 | Miles et al. |
| 9,757,151 B2 | 9/2017 | Weiman et al. |
| 9,782,158 B2 | 10/2017 | Nunley et al. |
| 9,788,822 B2 | 10/2017 | Miles et al. |
| 9,795,367 B1 | 10/2017 | Lee et al. |
| 9,795,371 B2 | 10/2017 | Miles et al. |
| 9,814,488 B2 | 11/2017 | Tatsumi |
| 9,820,729 B2 | 11/2017 | Miles et al. |
| 9,826,966 B2 | 11/2017 | Mast et al. |
| 9,826,968 B2 | 11/2017 | Miles et al. |
| 9,833,227 B2 | 12/2017 | Miles et al. |
| 9,848,861 B2 | 12/2017 | Miles et al. |
| 9,848,863 B2 | 12/2017 | Cryder et al. |
| 9,861,273 B2 | 1/2018 | Weiman |
| 9,888,859 B1 | 2/2018 | Spangler et al. |
| 9,918,709 B2 | 3/2018 | Sandhu |
| 9,924,859 B2 | 3/2018 | Lee et al. |
| 9,924,933 B2 | 3/2018 | Woolley et al. |
| 9,931,077 B2 | 4/2018 | Kaula et al. |
| 9,943,301 B2 | 4/2018 | Mast et al. |
| 9,993,239 B2 | 6/2018 | Karpowicz et al. |
| 10,034,662 B2 | 7/2018 | Bass et al. |
| RE46,978 E | 8/2018 | Simonson |
| 10,039,539 B2 | 8/2018 | Friedrich et al. |
| 10,130,348 B2 | 11/2018 | Cryder et al. |
| 10,166,018 B2 | 1/2019 | Hunt et al. |
| 2008/0249372 A1* | 10/2008 | Reglos ............... A61B 17/0293 600/245 |
| 2009/0036746 A1* | 2/2009 | Blackwell ........... A61B 17/0206 600/219 |

(56) References Cited

U.S. PATENT DOCUMENTS

| | | | |
|---|---|---|---|
| 2012/0245431 A1* | 9/2012 | Baudouin | A61B 17/0218 |
| | | | 600/213 |
| 2015/0018628 A1 | 1/2015 | Friedrich et al. | |
| 2016/0120532 A1 | 5/2016 | Donald | |
| 2017/0215856 A1 | 8/2017 | Martinelli et al. | |
| 2017/0238918 A1* | 8/2017 | Predick | A61B 17/7077 |
| 2018/0085105 A1* | 3/2018 | Kim | A61F 2/442 |
| 2019/0083081 A1* | 3/2019 | Ortiz | A61B 17/0206 |
| 2019/0274671 A1* | 9/2019 | Lauf | A61B 17/025 |

* cited by examiner

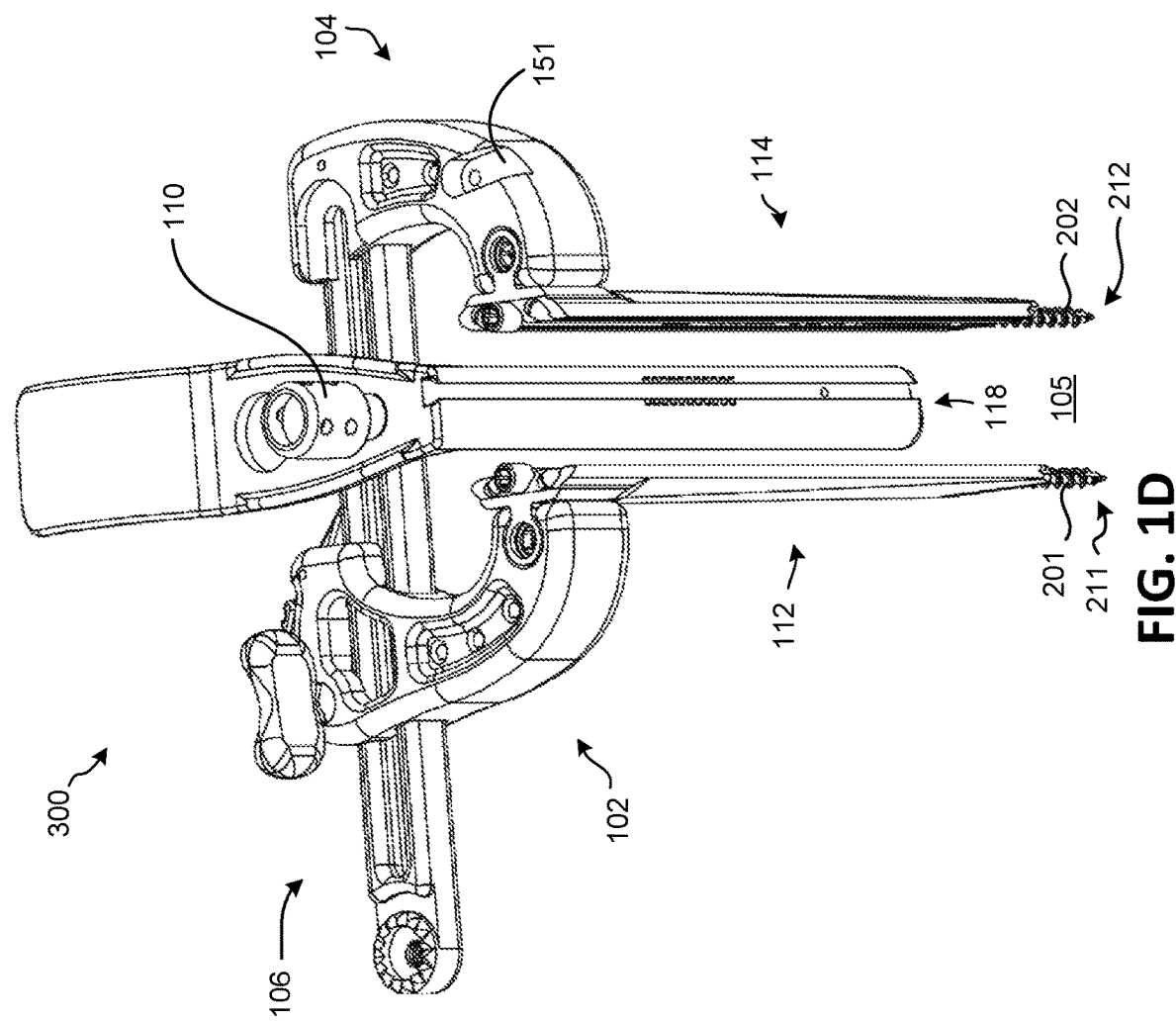

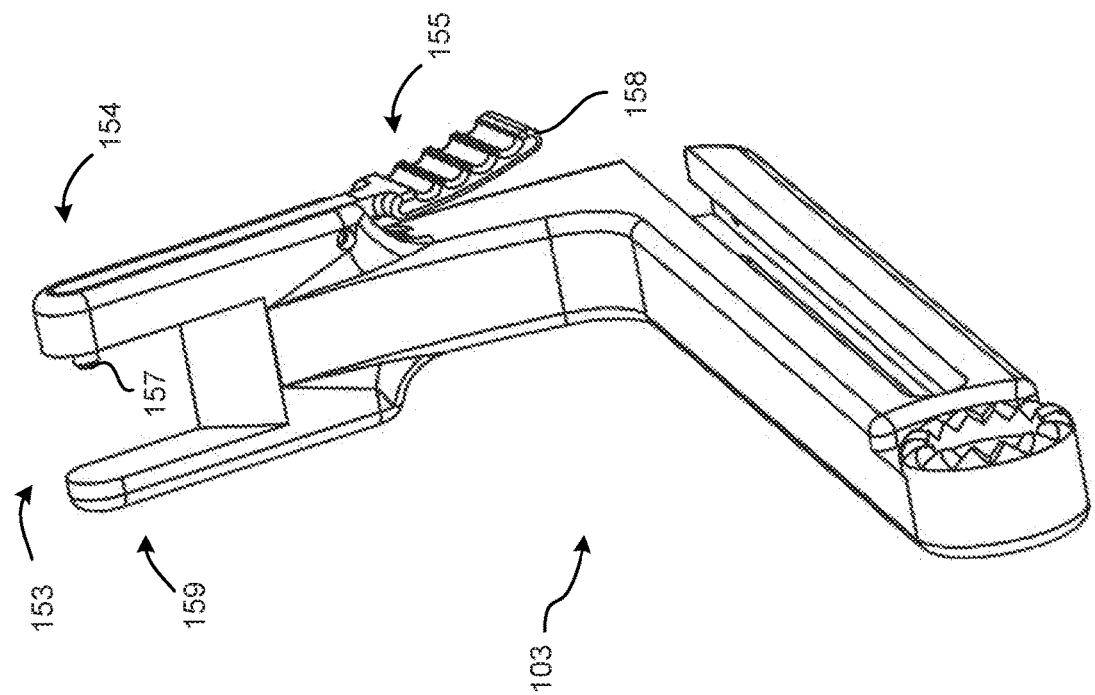
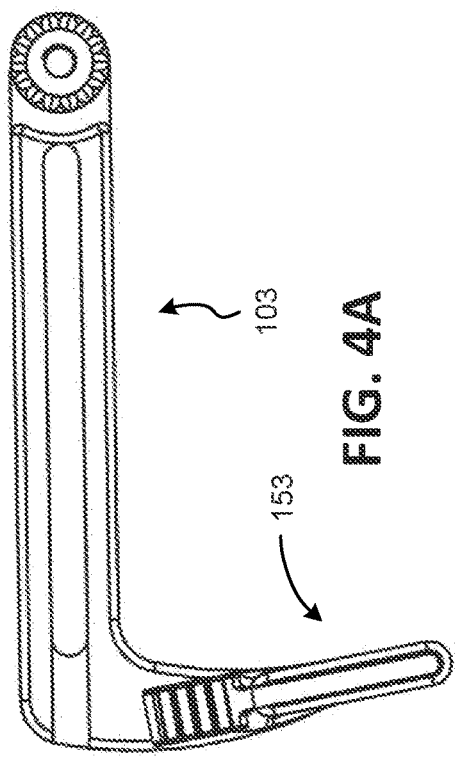
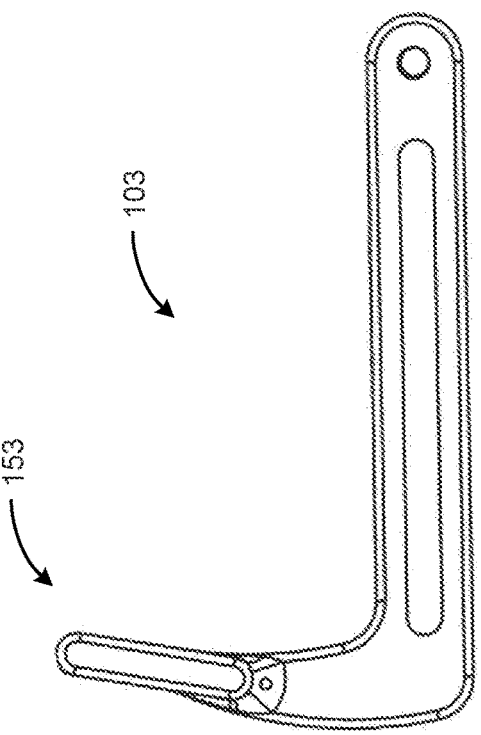

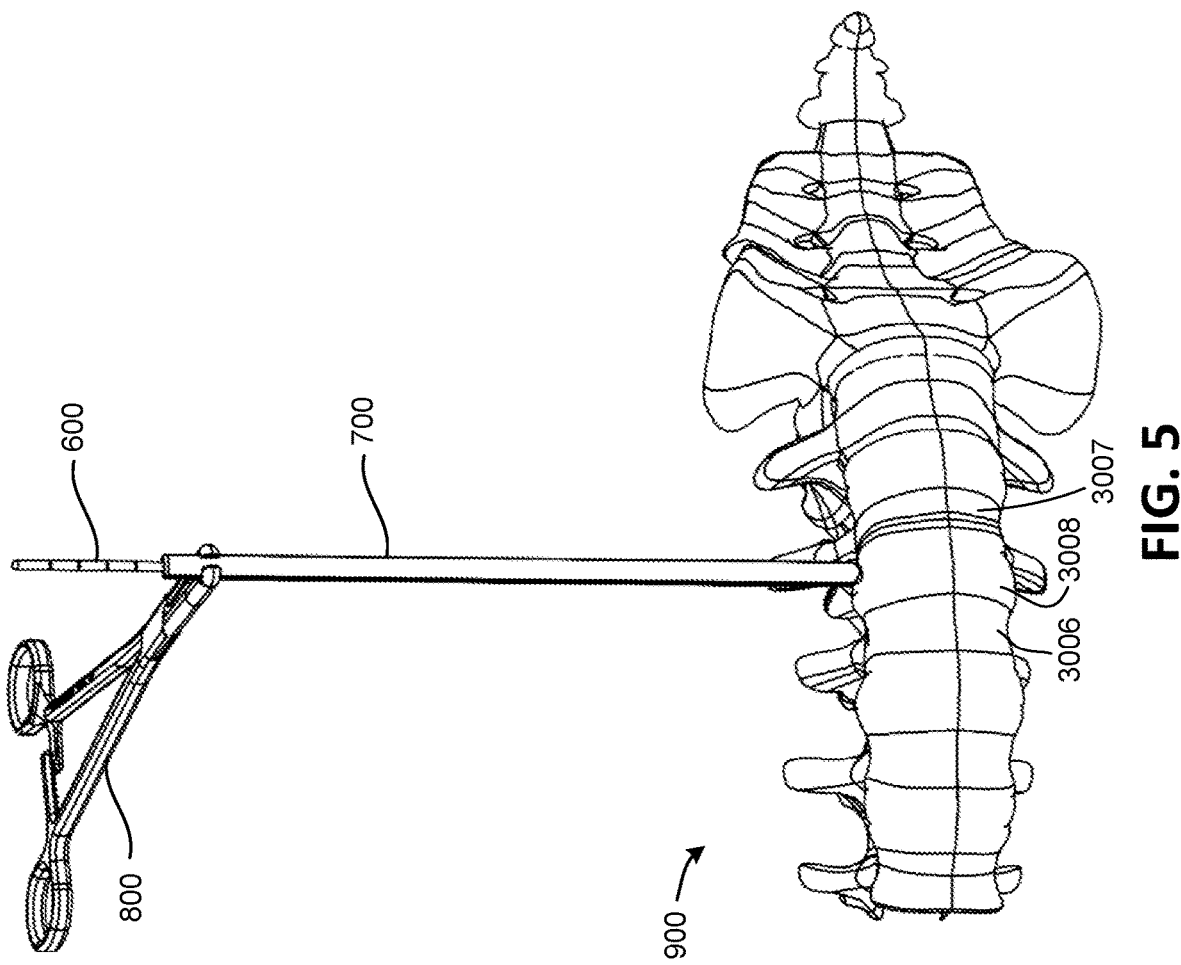

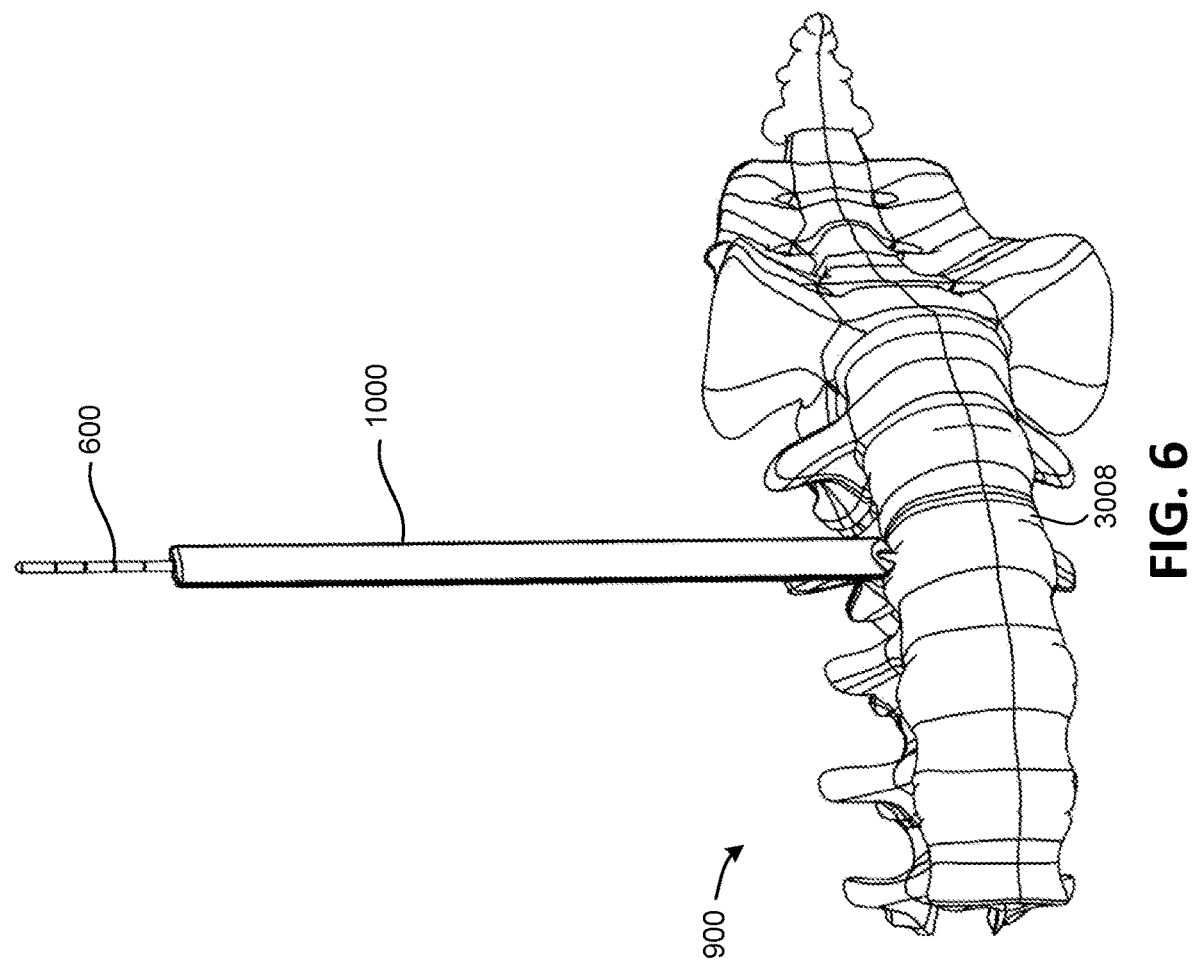

SYSTEMS AND METHODS FOR SURGICAL RETRACTION

TECHNICAL FIELD

The present disclosure relates to surgical instruments, systems, and methods. More specifically, the present disclosure relates to improved surgical instruments, systems, and methods for retracting tissues to facilitate implantation of intervertebral spacers between adjacent vertebral bodies in a patient.

BACKGROUND

Surgical procedures utilizing intervertebral spacers, artificial discs, and/or other implants can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an intervertebral spacer can be positioned within a space previously occupied by a disc between adjacent vertebral bodies. Such intervertebral spacers can help maintain a desired spacing between adjacent vertebrae and/or promote fusion between adjacent vertebrae. The use of bone graft and/or other materials within an intervertebral spacer can facilitate the fusion of adjacent vertebral bodies. One or more bone screws may also be utilized to help stabilize the intervertebral spacer during the fusion process.

Various approaches may be used to access the intervertebral space, such as anterior, posterior, lateral, and posterolateral approaches. Each of these approaches has its own set of advantages, drawbacks, and constraints. In each case, soft tissues impeding access to the intervertebral space must be moved out of the way to permit surgical instruments and implants to access the intervertebral space.

Existing retraction systems are encumbered by a number of disadvantages, including excess bulk or weight, poor visualization of the intervertebral space and/or the access pathway, and overall difficulty of operation. Such disadvantages can add to the expense, recovery time, and risk level associated with a surgical procedure.

SUMMARY

The various instruments, systems, and methods of the present disclosure have been developed in response to the present state of the art, and in particular, in response to the problems and needs in the art that have not yet been fully solved by currently available surgical instruments, systems, and methods.

According to one embodiment, a retractor system may be configured to provide access to a surgical site along an access pathway surrounded by tissue. The retractor system may have a first arm and a second arm connectable to the first arm such that the second arm is translatable along a first retraction direction relative to the first arm. The second arm may have a connection interface. The retractor system may further have a first retractor blade securable to the first arm such that the first retractor blade extends into the access pathway. The first retractor blade may have a first tissue engagement surface that engages the tissue. The retractor system may further have a second retractor blade securable to the second arm such that the second retractor blade extends into the access pathway, the second retractor blade comprising a second tissue engagement surface that engages the tissue. The retractor system may further have a third arm comprising a connection feature removably securable to the connection interface, and a third retractor blade securable to the third arm such that the third retractor blade extends into the access pathway to engage the tissue. The third retractor blade may have a third tissue engagement surface that engages the tissue, and may have a third cross-sectional shape oriented generally parallel to the first retraction direction.

The second arm and/or the third arm may have a locking mechanism with an actuator that can be actuated to move the locking mechanism between a locked configuration in which the connection feature is locked in place relative to the connection interface, and an unlocked configuration in which the connection feature is removable from the connection interface.

One of the connection interface and the connection feature may have a hole. The other of the connection interface and the connection feature may have a pin. In the locked configuration, the pin may reside in the hole. In the unlocked configuration, the pin may be displaced from the hole. The actuator may also have a lever coupled to the pin such that, in response to actuation of the lever, the lever moves the pin into and/or out of the hole.

The first arm may have a first blade interface. The first retractor blade may have a first arm interface securable to the first blade interface. One of the first blade interface and the first arm interface may have a socket with a partial wall defining a circumferential opening. The other of the first blade interface and the first arm interface may have a boss at one end of a bridge. The boss may be insertable into the socket such that the bridge resides in the circumferential opening.

The first blade interface may include the socket and the first arm interface may include the boss and the bridge. The boss may be insertable into the socket along an insertion direction that is generally parallel to the access pathway.

The retractor system may further have a guide dilator insertable into the access pathway to engage the tissue. The guide dilator may have a first side shaped to be coupled to the first retractor blade and a second side shaped to be coupled to the second retractor blade to guide insertion of the first retractor blade and the second retractor blade into the access pathway.

The first side may have a first slot shaped to receive the first retractor blade. The second side may have a second slot shaped to receive the second retractor blade.

Each of the first retractor blade and the second retractor blade may include a groove. The retractor system may further have a guide wire receivable in the grooves of the first retractor blade and the second retractor blade. The guide wire may have a distal end insertable into the surgical site along the access pathway. The retractor system may further have a first pin receivable in the grooves of the first retractor blade and the second retractor blade. The first pin may have a first distal end anchorable in a first bone proximate the surgical site. The retractor system may further have a second pin receivable in the grooves of the first retractor blade and the second retractor blade. The second pin may have a second distal end anchorable in a second bone proximate the surgical site.

The retractor system may further have a rack coupled to the first arm and the second arm. At least one of the first arm and the second arm may be slidably coupled to the rack to provide translation of the second arm relative to the first arm. The retractor system may further have a fourth retractor blade securable to the rack such that the fourth retractor blade extends into the access pathway to engage the tissue. The fourth retractor blade may have a fourth tissue engagement surface that engages the tissue. The fourth retractor blade may have a fourth cross-sectional shape oriented generally parallel to the first retraction direction. With the first retractor blade secured to the first arm, the second retractor blade secured to the second arm, the third retractor blade secured to the third arm, and the fourth retractor blade secured to the rack, the second retractor blade may be generally parallel to the first retractor blade, and the fourth retractor blade may be generally parallel to the third retractor blade and perpendicular to the first and second retractor blades.

The retractor system may further have a rack coupled to the first arm and the second arm. At least one of the first arm and the second arm may be slidably coupled to the rack to provide translation of the second arm relative to the first arm. The rack may have a mounting feature securable to an attachment arm fixedly mounted proximate the surgical site.

According to one embodiment, a retractor system may be configured to provide access to a surgical site along an access pathway surrounded by tissue. The retractor system may have a first arm and a second arm connectable to the first arm such that the second arm is translatable along a first retraction direction relative to the first arm. The second arm may have a connection interface. The retractor system may further have a first retractor blade securable to the first arm such that the first retractor blade extends into the access pathway. The first retractor blade may have a first tissue engagement surface that engages the tissue. The retractor system may further have a second retractor blade securable to the second arm such that the second retractor blade extends into the access pathway. The second retractor blade may have a second tissue engagement surface that engages the tissue. The first arm may have a first blade interface. The first retractor blade may have a first arm interface securable to the first blade interface. The first arm interface may be engageable with the first blade interface by moving the first arm interface, relative to the first blade interface, along an insertion direction generally parallel to the access pathway.

One of the first blade interface and the first arm interface may have a socket with a partial wall defining a circumferential opening. The other of the first blade interface and the first arm interface may have a boss at one end of a bridge. The boss may be insertable into the socket such that the bridge resides in the circumferential opening.

The first blade interface may have the socket and the first arm interface may have the boss and the bridge. The boss may be insertable into the socket along the insertion direction.

The socket may have a socket hole. The boss may have a boss hole. The retractor system may further have a fastener insertable into the boss hole and the socket hole along the insertion direction to secure the boss within the socket.

The retractor system may further have a third arm with a connection feature removably securable to the connection interface, and a third retractor blade securable to the third arm such that the third retractor blade extends into the access pathway to engage the tissue. The third retractor blade may have a third tissue engagement surface that engages the tissue. The third retractor blade may have a third cross-sectional shape oriented generally parallel to the first retraction direction. The retractor system may further have a rack coupled to the first arm and the second arm. At least one of the first arm and the second arm may be slidably coupled to the rack to provide translation of the second arm relative to the first arm. The retractor system may further have a fourth retractor blade securable to the rack such that the fourth retractor blade extends into the access pathway to engage the tissue. The fourth retractor blade may have a fourth tissue engagement surface that engages the tissue. The fourth retractor blade may have a fourth cross-sectional shape oriented generally parallel to the first retraction direction. With the first retractor blade secured to the first arm, the second retractor blade secured to the second arm, the third retractor blade secured to the third arm, and the fourth retractor blade secured to the rack, the second retractor blade may be generally parallel to the first retractor blade, and the fourth retractor blade may be generally parallel to the third retractor blade and perpendicular to the first and second retractor blades.

According to one embodiment, a retractor system may be configured to provide access to a surgical site along an access pathway surrounded by tissue. The retractor system may have a first arm and a second arm connectable to the first arm such that the second arm is translatable along a first retraction direction relative to the first arm. The second arm may have a connection interface. The retractor system may further have a first retractor blade securable to the first arm such that the first retractor blade extends into the access pathway. The first retractor blade may have a first tissue engagement surface that engages the tissue. The retractor system may further have a second retractor blade securable to the second arm such that the second retractor blade extends into the access pathway. The second retractor blade may have a second tissue engagement surface that engages the tissue. The retractor system may further have a guide dilator insertable into the access pathway to engage the tissue. The guide dilator may have a first side shaped to be coupled to the first retractor blade and a second side shaped to be coupled to the second retractor blade to guide insertion of the first retractor blade and the second retractor blade into the access pathway.

The first side may have a first slot shaped to receive the first retractor blade, and the second side may have a second slot shaped to receive the second retractor blade.

The retractor system may further have a guide wire with a distal end insertable into the surgical site along the access pathway. At least one of the first retractor blade and the second retractor blade may include a groove shaped to receive at least part of the guide wire therein.

The retractor system may further have a first pin receivable in the grooves of the first retractor blade and the second retractor blade. The first pin may have a first distal end anchorable in a first bone proximate the surgical site, and a second pin receivable in the grooves of the first retractor blade and the second retractor blade. The second pin may have a second distal end anchorable in a second bone proximate the surgical site.

The retractor system may further include a third arm with a connection feature removably securable to the connection interface, and a third retractor blade securable to the third arm such that the third retractor blade extends into the access pathway to engage the tissue. The third retractor blade may have a third tissue engagement surface that engages the tissue. The third retractor blade may have a third cross-sectional shape oriented generally parallel to the first retraction direction. The retractor system may further have a rack coupled to the first arm and the second arm. At least one of the first arm and the second arm may be slidably coupled to the rack to provide translation of the second arm relative to the first arm. The retractor system may further have a fourth retractor blade securable to the rack such that the fourth retractor blade extends into the access pathway to engage the tissue. The fourth retractor blade may have a fourth tissue engagement surface that engages the tissue. The fourth retractor blade may have a fourth cross-sectional shape oriented generally parallel to the first retraction direction. With the first retractor blade secured to the first arm, the second retractor blade secured to the second arm, the third retractor blade secured to the third arm, and the fourth retractor blade secured to the rack, the second retractor blade may be generally parallel to the first retractor blade, and the fourth retractor blade may be generally parallel to the third retractor blade and perpendicular to the first and second retractor blades.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 1D is a perspective view of a retractor system, according to another embodiment of the present disclosure;

FIG. 4A is a top view of a third retractor arm, according to one embodiment of the present disclosure;

FIG. 4B is a bottom view of the third retractor arm of FIG. 4A;

FIG. 4C is a perspective view of the third retractor arm of FIG. 4A;

FIG. 5 is a perspective view of a first dilator and a guide wire inserted proximate a spine;

FIG. 6 is a perspective view of a second dilator inserted over the guidewire of FIG. 5;

Figure 1A:
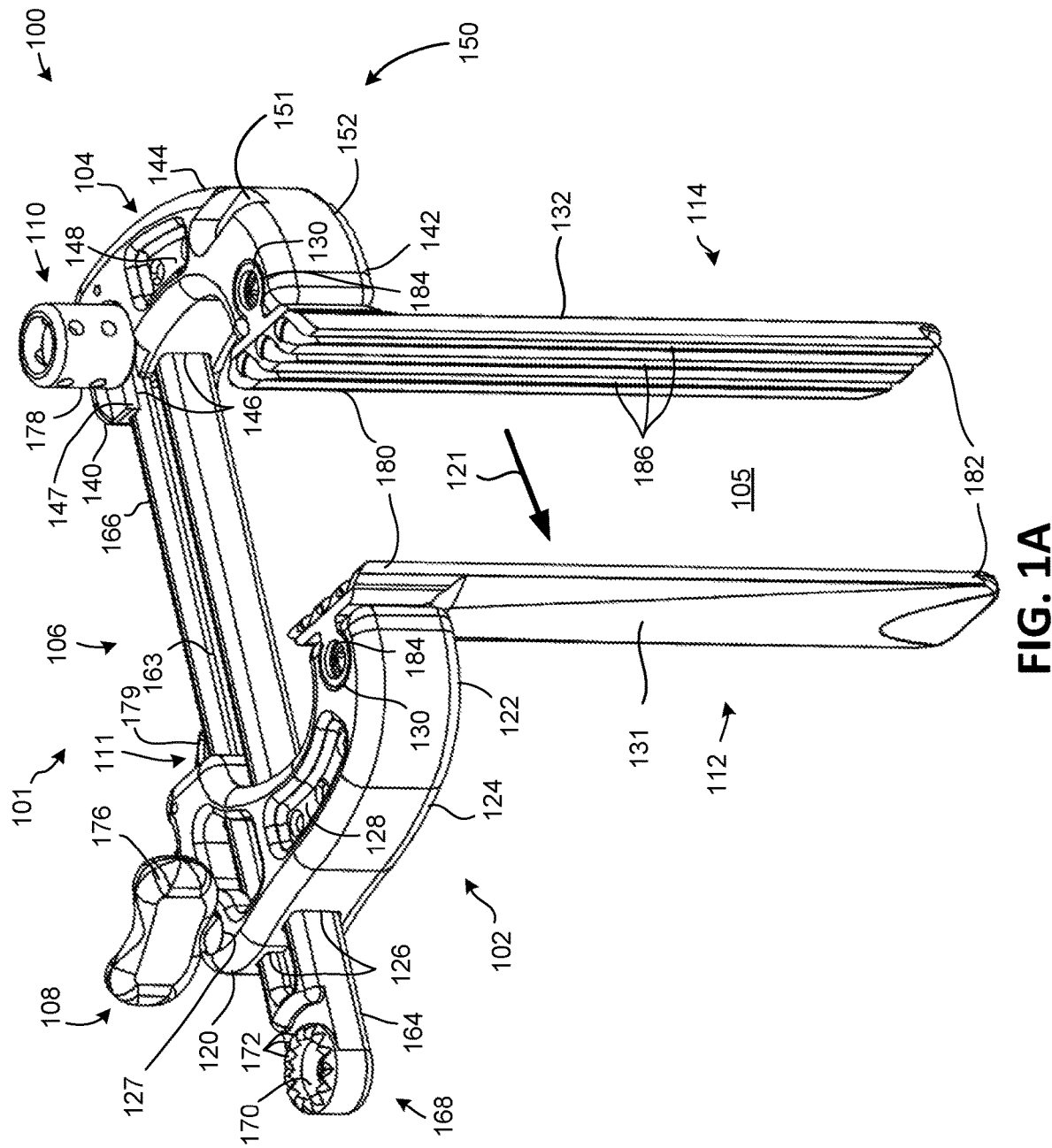
FIG. 1A is a perspective view of a retractor system, according to one embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior, or caudal, means toward the head. Inferior, or cephalad, means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

FIGS. 1A-1D illustrate various example retractor systems 100, 300, 400, according to embodiments of the present disclosure. A wide variety of surgical procedures may be performed with the aid of the retractor systems 100, 300, 400 disclosed herein. For example, in some embodiments a surgical procedure may include the preparation of an interbody space between adjacent vertebral bodies of a spine and/or the implantation of a fusion cage into the interbody space in order to promote interbody fusion between the adjacent vertebral bodies. In a particular embodiment, the retractor systems 100, 300, 400 may be utilized to provide a lateral access pathway to the interbody space between the adjacent vertebral bodies.

FIGS. 2A-4C illustrate some of the individual components that may correspond to the retractor systems 100, 300, 400 shown in FIGS. 1A-1D. For example, FIGS. 2A-2F illustrate various views of a retractor blade that may be utilized in each of the retractor systems 100, 300, 400; FIGS. 3A-3C illustrate various views of an optional blade, a blade extender 119, and/or a disc shim 117 which may be utilized in the retractor systems 300, 400; and FIGS. 4A-4C illustrate various views of an optional third arm that may be utilized in the retractor system 400.

FIG. 1A illustrates a perspective view of the retractor system 100. The retractor system 100 may comprise a retractor 101 having a first arm 102, a second arm 104, a rack 106, a first rack coupling feature 108, a second rack coupling feature 110, a locking feature 111, a first retractor blade 112, and a second retractor blade 114. The retractor 101 may be designed such that the first and second arms 102, 104 retain the first and second retractor blades 112, 114 along an access pathway 105 that lies in between the first and second retractor blades 112, 114. In this manner, the access pathway 105 may define a space through soft tissue (not shown) leading to a surgical site within a patient where a surgical procedure may be performed. The first arm 102 and the second arm 104 may be configured to spread apart from each other to move the first retractor blade 112 and the second retractor blade 114 away from each other to widen the access pathway 105 and provide sufficient access to the surgical site.

The first arm 102 and the second arm 104 may be coupled to the rack 106 such that the first arm 102 and the second arm 104 may translate closer together or further apart. Specifically, the first arm 102 may be coupled to the rack 106 by the first rack coupling feature 108, and the second arm 104 may be coupled to the rack 106 via a pin (not shown). The first rack coupling feature 108 may be adjustable to translate the first arm 102 along the rack 106, while the second arm 104 may be secured at a stationary position along the rack 106. Thus, the first rack coupling feature 108 may be used to move the first arm 102 toward or away from the second arm 104 along the rack 106. In this manner, the first and second arms 102, 104 may be translatable along a first retraction direction 121 relative to each other. The locking feature 111 may also be utilized to lock the relative positions of the first arm 102 and the second arm 104 until further adjustment is desired.

The first arm 102 may have a first end 120, a second end 122, and an intermediate portion 124. The first end 120 may be movably coupled to the rack 106 with the first rack coupling feature 108, as mentioned above. Thus, the first end 120 may have a set of apertures 126 that receive the rack 106 and a hole 127 that may receive the first rack coupling feature 108. The intermediate portion 124 may have a recess 128 that serves to reduce the weight and volume of the first arm 102. The second end 122 may have a blade interface 130 that is securable to the first retractor blade 112 so that the first arm 102 is able to securely hold the first retractor blade 112 against forces exerted on a first tissue engagement surface 131 of the first retractor blade 112 as it is pressed against tissues that surround the access pathway 105.

Similarly, the second arm 104 may have a first end 140, a second end 142, and an intermediate portion 144. The first end 140 may be secured to the rack 106 with a pin (not shown), as mentioned above. Thus, the first end 140 may have a set of apertures 146 that receive the rack 106, and a slot 147 that receives the second rack coupling feature 110. The intermediate portion 144 may have a recess 148 that serves to reduce the weight and volume of the second arm 104. The second end 142 may have a blade interface 130 that is securable to the second retractor blade 114 so that the second arm 104 is able to securely hold the second retractor blade 114 against forces exerted against a second tissue engagement surface 132 of the second the second arm 104 as it is pressed against tissues that surround the access pathway 105.

The intermediate portion 144 of the second arm 104 may also include a connection interface 150 designed to facilitate attachment of the third arm 103 to the second arm 104 via a connection feature 153 of the third arm 103, as shown in FIGS. 1C and 4A-4C. In some embodiments, the connection interface 150 may have a first recess 151 and a second recess 152 that can maintain an orientation for the third arm 103 relative to the second arm 104, and a hole 156 in which a pin 157 (see FIG. 4C) of the third arm 103 may be anchored. The third arm 103 may also include an actuator 155 comprising a lever 158 coupled to an actuator arm 154. The connection feature 153 of the third arm 103 may comprise the actuator arm 154 and a lower arm 159 opposite the actuator arm 154, as shown in FIG. 4C. The actuator arm 154 may be received within the first recess 151 formed in the intermediate portion 144 of the second arm 104, and the lower arm 159 may be received within the second recess 152 formed in the intermediate portion 144 of the second arm 104 to removably secure the third arm 103 to the intermediate portion 144 of the second arm 102. The pin 157 may also be coupled to the actuator arm 154. In a locked configuration, the pin 157 may reside in the hole 156. In an unlocked configuration, the pin 157 may be displaced from the hole 156 such that the third arm 103 may be decoupled from the second arm 104. Thus, the lever 158 may be actuated to move the actuator arm 154, which may in turn move the pin 157 into and/or out of the hole. In this manner, the actuator 155 may form a locking mechanism that can be actuated to move the locking mechanism between a locked configuration in which the connection feature 153 is locked in place relative to the connection interface 150, and an unlocked configuration in which the connection feature 153 is removable from the connection interface 150. However, it will also be understood that in other embodiments one of the connection interface 150 and the connection feature 153 may comprise the hole 156 and the other of the connection interface 150 and the connection feature 153 may comprise the pin 157.

The rack 106 may have a first end 164 and a second end 166. The first end 164 may be shaped to define a mounting feature 168 that can optionally be used to secure the retractor systems 100, 300, 400 at a stationary position relative to an operating table through the use of an attachment arm 9000 or the like (e.g., see FIG. 24). In this manner, the mounting feature may be securable to the attachment arm 9000, which itself may be fixedly mounted proximate the surgical site via a clamp base 9020. The mounting feature 168 may be shaped to facilitate such secure attachment, and may thus have a hole 170 surrounded by teeth 172. The attachment arm 9000 may also have a corresponding mounting feature 9068 that may include a bolt, boss, or other protrusion that extends through the hole 170 of the mounting feature 168, and a plate or other surface that is pressed against the teeth 172 by virtue of the mounting. The teeth 172 may abut the plate or other surface to prevent the retractor system 100, 300, 400 from rotating relative to the attachment arm 9000. The plate or other surface of the attachment arm 9000 may be textured or may even have teeth that can mesh with the teeth 172 of the mounting feature 168 in order to help prevent such relative rotation.

Figure 1B:
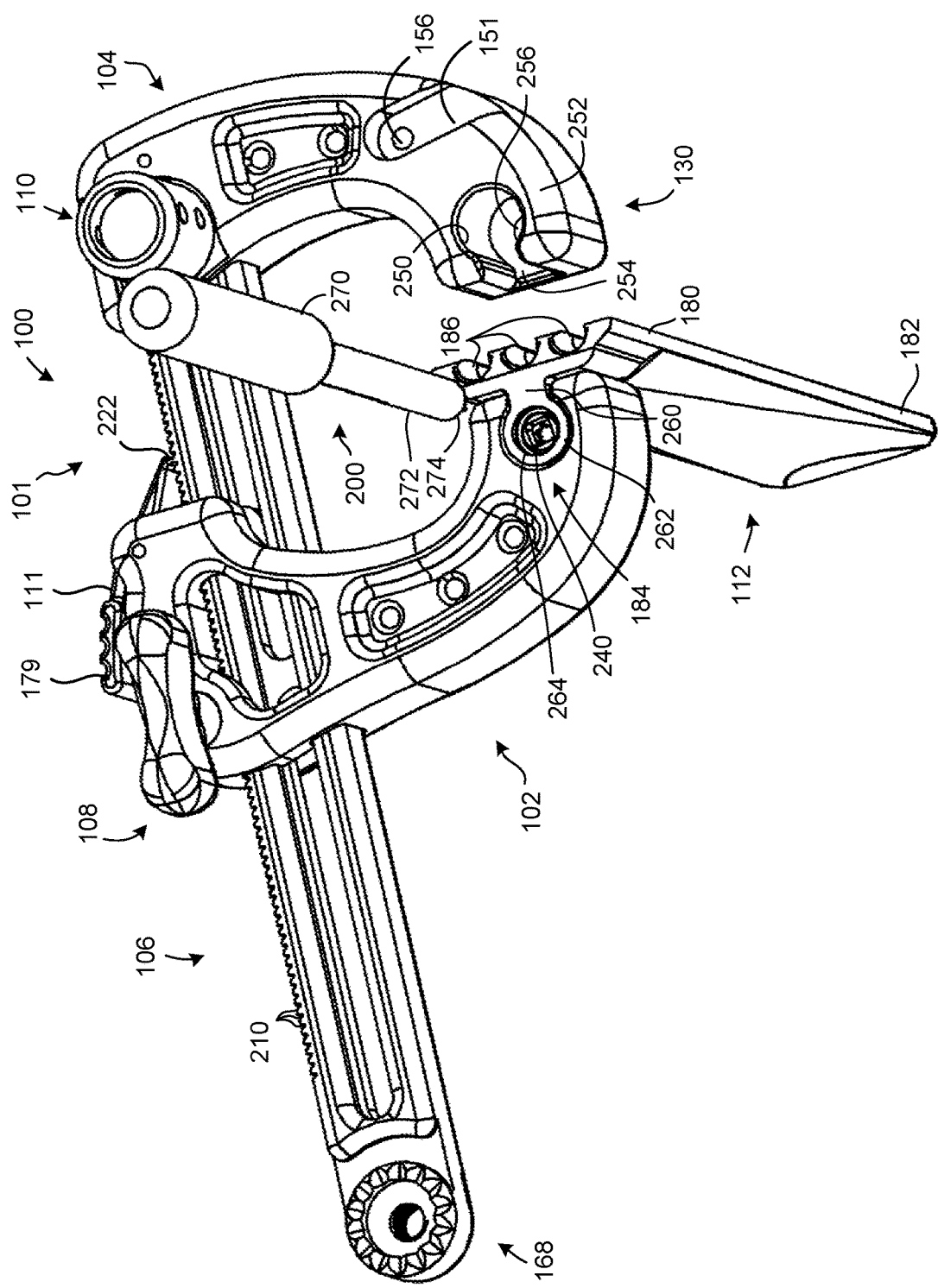
FIG. 1B is a top perspective view of the retractor system of FIG. 1A during assembly.

FIG. 1B is an alternative perspective view of the retractor system 100 of FIG. 1A during assembly (with the second retractor blade 114 removed) showing a driver 200 that may be utilized to secure the first retractor blade 112 to the first arm 102 and secure the second retractor blade 114 to the second arm 104, according to some embodiments. Further features of the retractor system 100 will now be shown and described in connection with FIGS. 1A and 1B.

As shown in FIG. 1B, the rack 106 may include teeth 210 extending along some portion of the length of the rack 106 to facilitate adjustment of the position of the first arm 102 along the rack 106.

The first rack coupling feature 108 may be designed to interface with the teeth 210 to provide such adjustment. Thus, for example, the first rack coupling feature 108 may have a wing-shaped handle 176 that can be easily rotated by a user. The wing-shaped handle 176 may be secured to a shaft (not visible in FIGS. 1A and 1B) passing through the hole 127 of the first arm 102. The shaft may be secured to a pinion (not visible in FIGS. 1A and 1B) with teeth that may mesh with the teeth 210 of the rack 106 to define a rack-and-pinion system. Thus, rotation of the wing-shaped handle 176 may rotate the pinion and urge the first arm 102 to move along the rack 106.

Figure 1C:
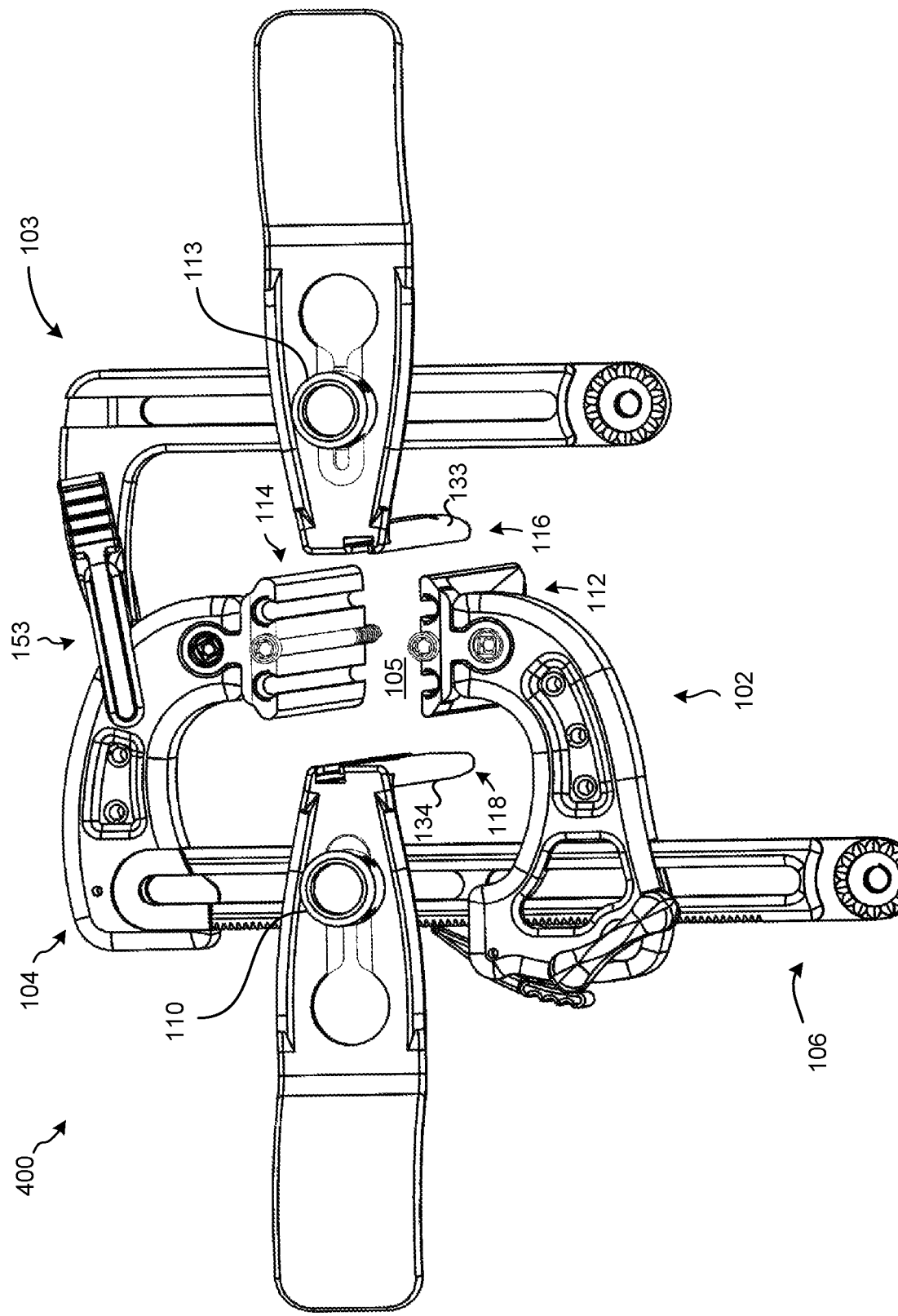
FIG. 1C is a top perspective view of a retractor system, according to another embodiment of the present disclosure.
Figure 2A:
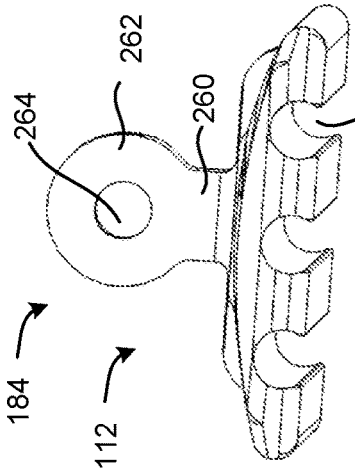
FIG. 2A is a left side view of a retractor blade, according to one embodiment of the present disclosure.
Figure 2B:
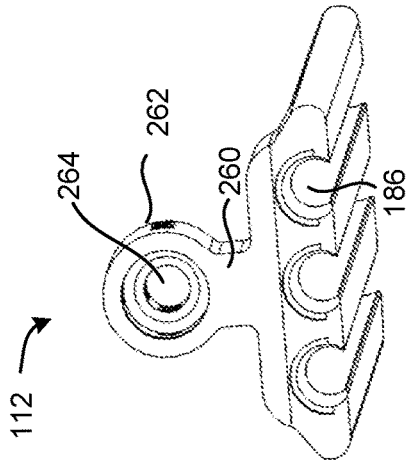
FIG. 2B is a right side view of the retractor blade of FIG. 2A.
Figure 2C:
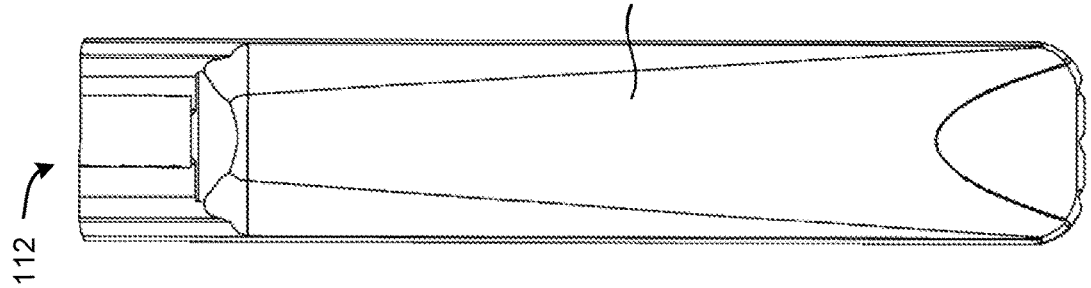
FIG. 2C is a front view of the retractor blade of FIG. 2A.
Figure 2D:
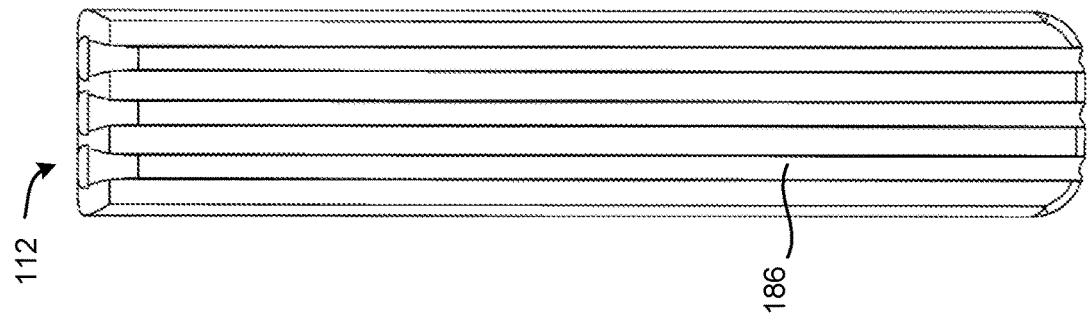
FIG. 2D is a rear view of the retractor blade of FIG. 2A.
Figure 2E:
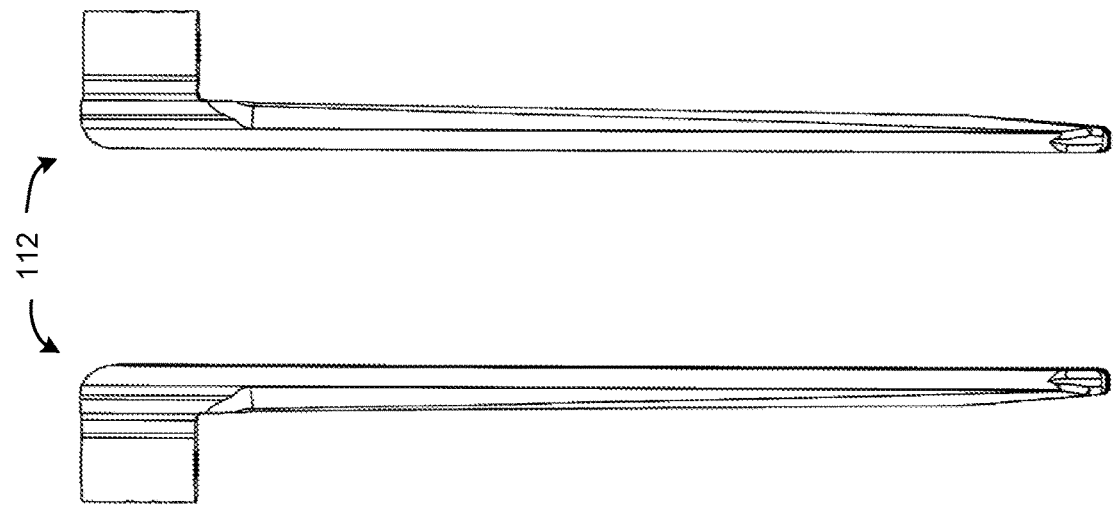
FIG. 2E is a bottom perspective view of the retractor blade of FIG. 2A.
Figure 2F:
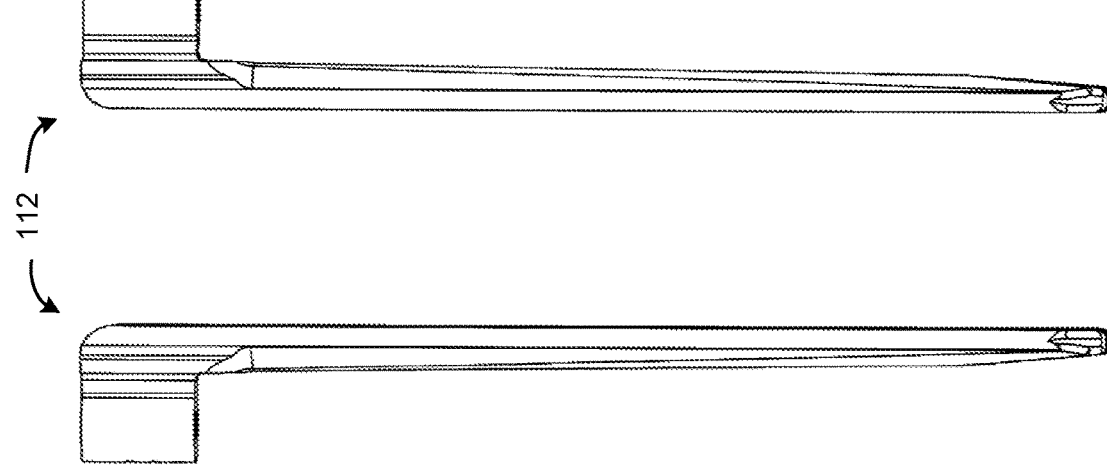
FIG. 2F is a top perspective view of the retractor blade of FIG. 2A.

The second rack coupling feature 110 may be designed to secure an optional blade to the rack 106, as shown in FIGS. 1C and 1D. The second rack coupling feature 110 may include a knob 178 and a threaded boss (not visible in FIGS. 1A and 1B) that can be inserted into the slot 147 of the second arm 104 and/or into the slot 163 of the rack 106 and rotated into engagement with the rack 106 to secure the optional blade into a desired position along the rack 106, as shown in FIG. 1C.

The locking feature 111 may be utilized to selectively lock the first arm 102 in place on the rack 106 to preventing further (or accidental) adjustment until the locking feature 111 is unlocked. The locking feature 111 may thus have a locked configuration in which the locking feature 111 prevents motion of the first arm 102 along the rack 106, and an unlocked configuration in which the locking feature 111 allows the first arm 102 to move along the rack 106. The locking feature 111 may interface with the teeth 210 arranged along the rack 106. For example, the locking feature 111 may include a lever 179 at a first end of the locking feature 111 and a tooth 222 at a second end of the locking feature 111. The locking feature 111 may include a spring (not shown) that may bias the tooth 222 toward the teeth 210 of the rack 106 to prevent the first arm 102 from translating along the rack 106, thereby retaining the locking feature 111 in a locked configuration. However, a user may actuate the lever 179 to overcome the biasing force of the spring and pull the tooth 222 out of engagement with the teeth 210 of the rack 106 to allow the first arm 102 to translate along the rack 106.

The first arm 102 and the second arm 104 may be shaped such that the second end 122 of the first arm 102 curves toward the second end 142 of the second arm 104, thereby keeping the first retractor blade 112 and the second retractor blade 114 at a desired relative displacement while ensuring that the first arm 102 and the second arm 104 do not interfere with the access pathway 105.

The first retractor blade 112 and the second retractor blade 114 may be designed to securely attach to the second end 122 of the first arm 102 and the second end 142 of the second arm 104, respectively. The first retractor blade 112 and the second retractor blade 114 may each have a proximal end 180 secured to the corresponding one of the first arm 102 and the second arm 104, and a distal end 182 that extends into the access pathway 105, proximate the surgical site. The proximal end 180 of each of the first retractor blade 112 and the second retractor blade 114 may have an arm interface 184 that mates with the blade interface 130 of the corresponding one of the first arm 102 and the second arm 104 to facilitate attachment.

Each of the first retractor blade 112 and the second retractor blade 114 may further have one or more (for example, three) grooves 186 that extend along the length of the first retractor blade 112 and the second retractor blade 114, from the proximal end 180 to the distal end 182. The grooves 186 may be used to anchor the first retractor blade 112 and the second retractor blade 114 to bone, for example, with pins (e.g., the first pin 201 and the second pin 202 shown in FIG. 1D) and/or a guide wire 600 (e.g., see FIG. 14). The grooves 186 may also be utilized to retain other implements that can facilitate the surgical procedure, such as one or more light sources 8000 (e.g., see FIG. 20), a neural monitoring probe (not shown), etc.

Continuing with FIG. 1B, the first retractor blade 112 and the second retractor blade 114 may be secured to the first arm 102 and the second arm 104 via attachment of the blade interface 130 of each of the first arm 102 and the second arm 104 to the arm interface 184 of the corresponding one of the first retractor blade 112 and the second retractor blade 114, with the additional use of a fastener 240. Each blade interface 130 and arm interface 184 may mate together in a manner that prevents relative translation and rotation between the first arm 102 and the first retractor blade 112, and between the second arm 104 and the second retractor blade 114. Advantageously, the mating of the blade interface 130 with the arm interface 184 may prevent relative rotation between the first arm 102 and the first retractor blade 112, and between the second arm 104 and the second retractor blade 114, without requiring the use of the fastener 240.

More precisely, each blade interface 130 may have a socket 250 defined by a partial wall 252, which may define a circumferential opening 254. As defined herein, a "circumferential opening" may include any opening in a circumference that breaks the circumference from fully encircling a central feature (e.g., the socket 250). The term "circumferential opening" does not limit the central feature from having shapes other than a round circumference. For example, the central feature may have any suitable shape, such as a polygonal shape, etc. The socket 250 may have a socket hole 256 to receive a distal shaft portion of the fastener 240 (not visible in FIG. 1B). The socket hole 256 may also include threads that engage corresponding threads on the distal shaft portion of the fastener 240.

Each arm interface 184 may have a bridge 260 protruding from the proximal end 180 of the first retractor blade 112 or the second retractor blade 114, and a boss 262 positioned at the distal end of the bridge 260. The boss 262 may be sized to slide into engagement with the socket 250 along a longitudinal axis of the socket 250, such that the bridge 260 slides into the circumferential opening 254. In this manner, the boss 262 may be insertable into the socket 250 along an insertion direction that is generally parallel to the access pathway 105. The boss 262 may have a boss hole 264 (see FIGS. 2E and 2F) that receives a proximal shaft portion (not visible) of the fastener 240. The boss hole 264 may be smooth, and the proximal shaft portion of the fastener 240 may be similarly smooth to permit the proximal shaft portion of the fastener 240 to rotate as the distal shaft portion of the fastener 240 rotates into engagement with the socket hole 256 formed in the socket 250.

However, it will be understood that in other embodiments one of the blade interface 130 and the arm interface 184 may comprise the socket 250 defined by the partial wall 252 defining the circumferential opening 254, and the other of the blade interface 130 and the arm interface 184 may comprise the boss 262 at one end of the bridge 260, such that the boss 262 may be insertable into the socket 250 and the bridge 260 may reside in the circumferential opening 254.

The driver 200 may be used to secure the first retractor blade 112 and the second retractor blade 114 to the first arm 102 and the second arm 104 respectively. The driver 200 may have a handle 270 that is of a size and shape suitable for gripping, and a shaft 272 extending from the handle 270. A drive feature 274 (for example, a hexagonal boss, etc.) at a distal end of the shaft 272 may mate with a corresponding feature (for example, a hexagonal recess) formed in the fastener 240.

The first retractor blade 112 may be secured to the first arm 102 by, first, moving the boss 262 of the first retractor blade 112 into the socket 250, such that the bridge 260 of the first retractor blade 112 seats in the circumferential opening 254 of the first arm 102. Then, the fastener 240 may be inserted such that its distal shaft portion enters the socket hole 256 formed in the socket 250 of the first arm 102, and the proximal shaft portion of the fastener 240 enters the boss hole 264 formed in the boss 262 of the first retractor blade 112. As mentioned previously, the socket 250 may retain the boss 262 in such a manner that, when assembled, relative rotation between the first retractor blade 112 and the first arm 102 may be prevented.

Finally, the driver 200 may be used to tighten the fastener 240 to compress the boss 262 against the interior of the socket 250, thereby completing attachment of the first retractor blade 112 to the first arm 102. The second retractor blade 114 may be secured to the second arm 104 in a similar manner.

FIGS. 1C and 1D illustrate perspective views of additional retractor systems 300, 400, according to embodiments of the present disclosure. The retractor systems 300 and 400 may generally comprise the retractor system 100 of FIGS. 1A and 1B in combination with additional components coupled thereto. For example, the retractor system 400 of FIG. 1C may include a third arm 103 coupled with the second arm 104 via a connection feature 153 engaged with the connection interface 150 of the second arm. The retractor system 400 may also include a third retractor blade 116 coupled to the third arm 103 via a third rack coupling feature 113. Each of the retractor systems 300, 400 may also include a fourth retractor blade 118 coupled to the rack 106 via the second rack coupling feature 110.

The third retractor blade 116 may be securable to the third arm 103 such that the third retractor blade 116 extends into the access pathway 105 to engage soft tissue with a third tissue engagement surface 133. The third retractor blade 116 may have a cross-sectional shape that is oriented generally parallel to the first retraction direction 121.

Likewise, the fourth retractor blade 118 may be securable to the rack 106 such that the fourth retractor blade 118 extends into the access pathway 105 to engage soft tissue with a fourth tissue engagement surface 134. The fourth retractor blade 118 may also have a cross-sectional shape that is oriented generally parallel to the first retraction direction 121.

As shown in FIG. 1C, with the first retractor blade 112 secured to the first arm 102, the second retractor blade 114 secured to the second arm 104, the third retractor blade 116 secured to the third arm 103, and the fourth retractor blade 118 secured to the rack 106, the second retractor blade 114 may be generally parallel to the first retractor blade 112, and the fourth retractor blade 118 may be generally parallel to the third retractor blade 116 and perpendicular to the first and second retractor blades 112, 114.

Figure 3C:
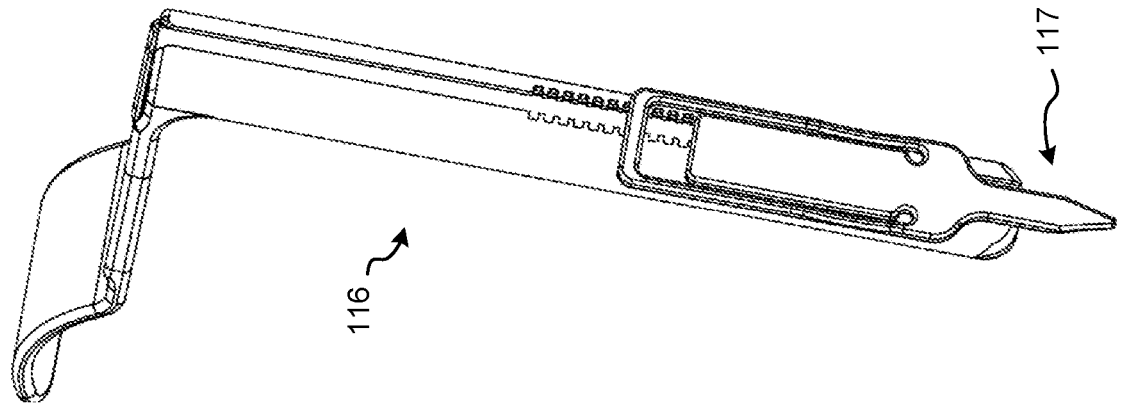
FIG. 3C is a perspective view of the retractor blade of FIG. 3A coupled to a disc shim, according to another embodiment of the present disclosure.
Figure 3B:
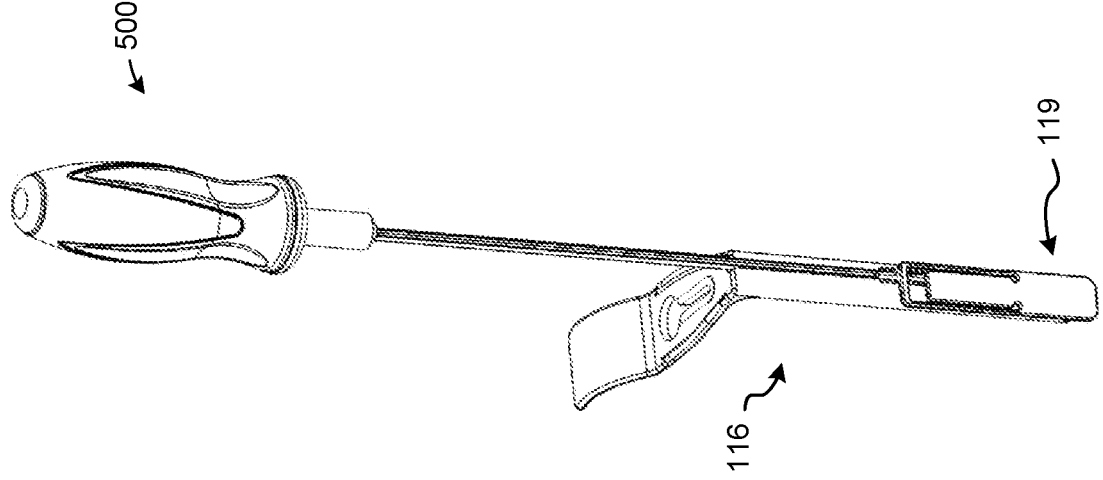
FIG. 3B is a perspective view of the retractor blade and blade extender of FIG. 3A during assembly via a disc shim tool.
Figure 3A:
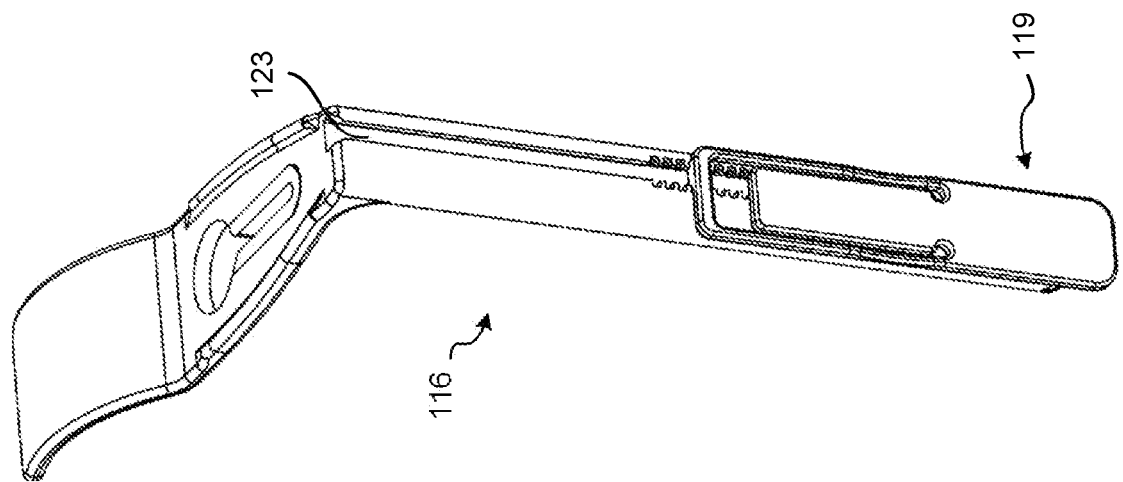
FIG. 3A is a perspective view of a retractor blade coupled to a blade extender, according to one embodiment of the present disclosure.

FIGS. 3A-3C illustrate the third retractor blade 116 (and/or the fourth retractor blade 118, which may be similarly shaped) of FIGS. 1C and 1D in isolation. Specifically, FIG. 3A is a perspective view of the third retractor blade 116 coupled to a blade extender 119; FIG. 3B is a perspective view of the third retractor blade 116 and blade extender 119 of FIG. 3A during assembly via a disc shim tool 500; and FIG. 3C is a perspective view of the third retractor blade 116 FIG. 3A coupled to a disc shim 117.

The blade extender 119 and the disc shim 117 may each be utilized with the third and/or fourth retractor blades 116, 118 in order to: (1) extend the length of the third and/or fourth retractor blades 116, 118 with the blade extender 119; and (2) increase access to an interbody space and/or help secure the third and/or fourth retractor blades 116, 118 to the spine of the patient by securing the disc shim 117 in between two adjacent vertebral bodies of the patient. The blade extender 119 and the disc shim 117 may be coupled to the third and/or fourth retractor blades 116, 118 via the T-slot 123 that is formed in the third and/or fourth retractor blades 116, 118. The blade extender 119 and the disc shim 117 may also include a ratcheting mechanism (not visible in FIGS. 3A-3C) that may further couple the blade extender 119 and the disc shim 117 to the third and/or fourth retractor blades 116, 118 at a plurality of different positions along the third and/or fourth retractor blades 116, 118. The disc shim tool 500 may be utilized to selectively place the blade extender 119 and the disc shim 117 at one of the plurality of different positions along the third and/or fourth retractor blades 116, 118, and/or completely remove the blade extender 119 and the disc shim 117 from the third and/or fourth retractor blades 116, 118.

FIGS. 5-20 illustrate how the retractor systems 100, 300, 400 of the present disclosure may be inserted proximate a spine 900 of a patient using a lateral approach, as one non-limiting example of the present disclosure.

FIG. 5 illustrates a perspective view of a first dilator 700 inserted laterally through a psoas muscle (not shown) of the patient proximate a target interbody space 3008 between a first vertebral body 3006 and a second vertebral body 3007 of the spine 900. The first dilator 700 may be guided to the interbody space 3008 via any imaging technique known in the art. The guide wire 600 may be placed through the first dilator 700 into the interbody space 3008 after the first dilator 700 has been placed proximate the interbody space 3008. The dilator holder 800 may be utilized to hold the first dilator 700 (or other instrument components) during an imaging process (e.g., fluoroscopic imaging, etc.) for increased safety to the surgeon. The dilator holder 800 may also be utilized to rotate the first dilator 700 or other instrument components, as will be discussed below in more detail.

FIG. 6 is a perspective view of a second dilator 1000 inserted laterally proximate the target interbody space 3008 in a first orientation. The second dilator 1000 may be larger than the first dilator 700 and may be inserted over the guide wire 600. The second dilator 1000 may be inserted through a psoas muscle (not shown) of the patient above the interbody space 3008 in the first orientation (as shown in FIG. 6) in order to split the fibers of the psoas muscle longitudinally and minimize trauma to the psoas muscle.

Figure 7:
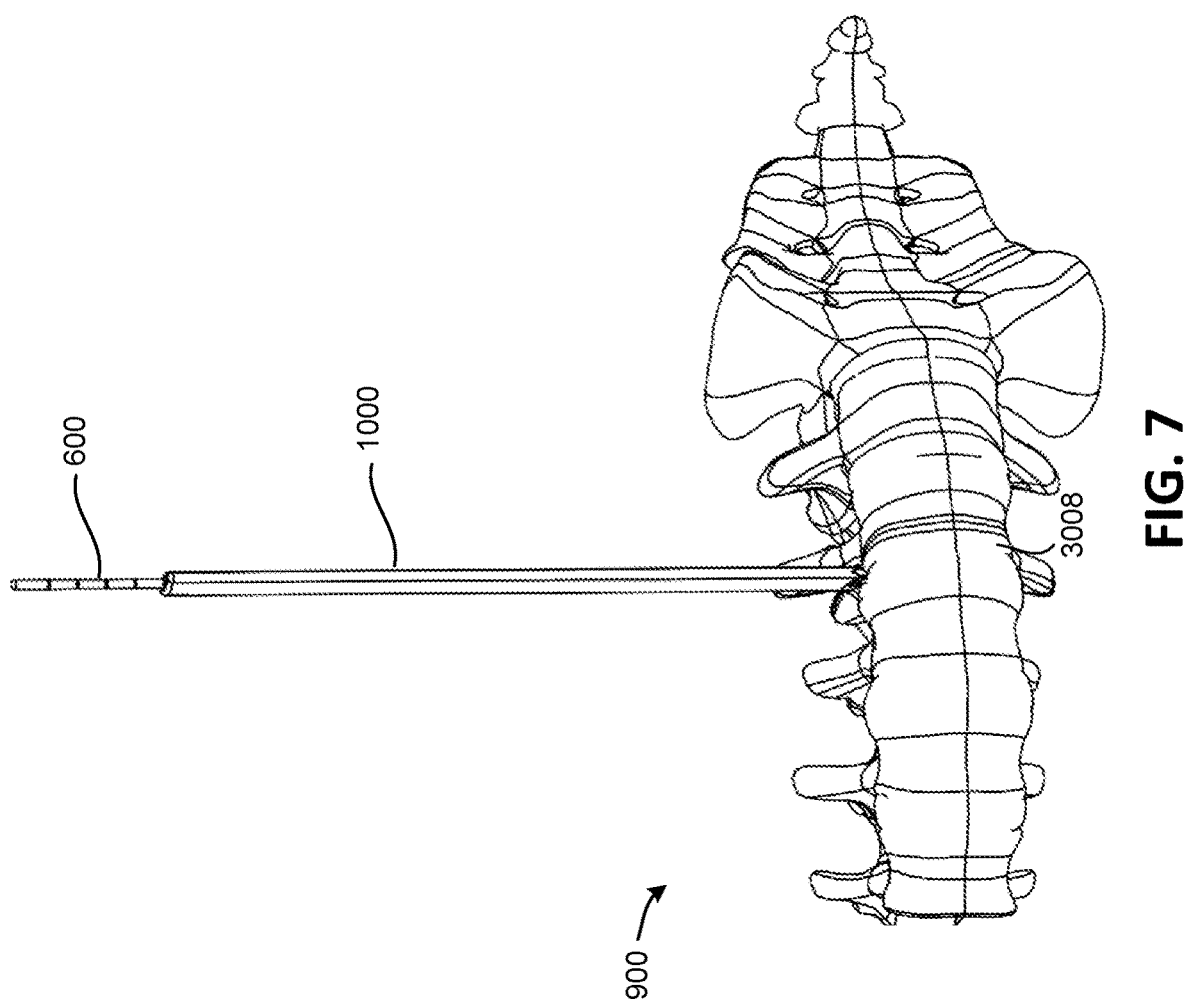
FIG. 7 is a perspective view of the second dilator of FIG. 6 rotated 90 degrees.

FIG. 7 is a perspective view of the second dilator 1000 of FIG. 6 after it has been rotated 90 degrees. In this manner, the fibers of the psoas muscle may be retracted apart from each other with minimal trauma to the psoas muscle as the second dilator 1000 is rotated 90 degrees from the first orientation.

Figure 8:
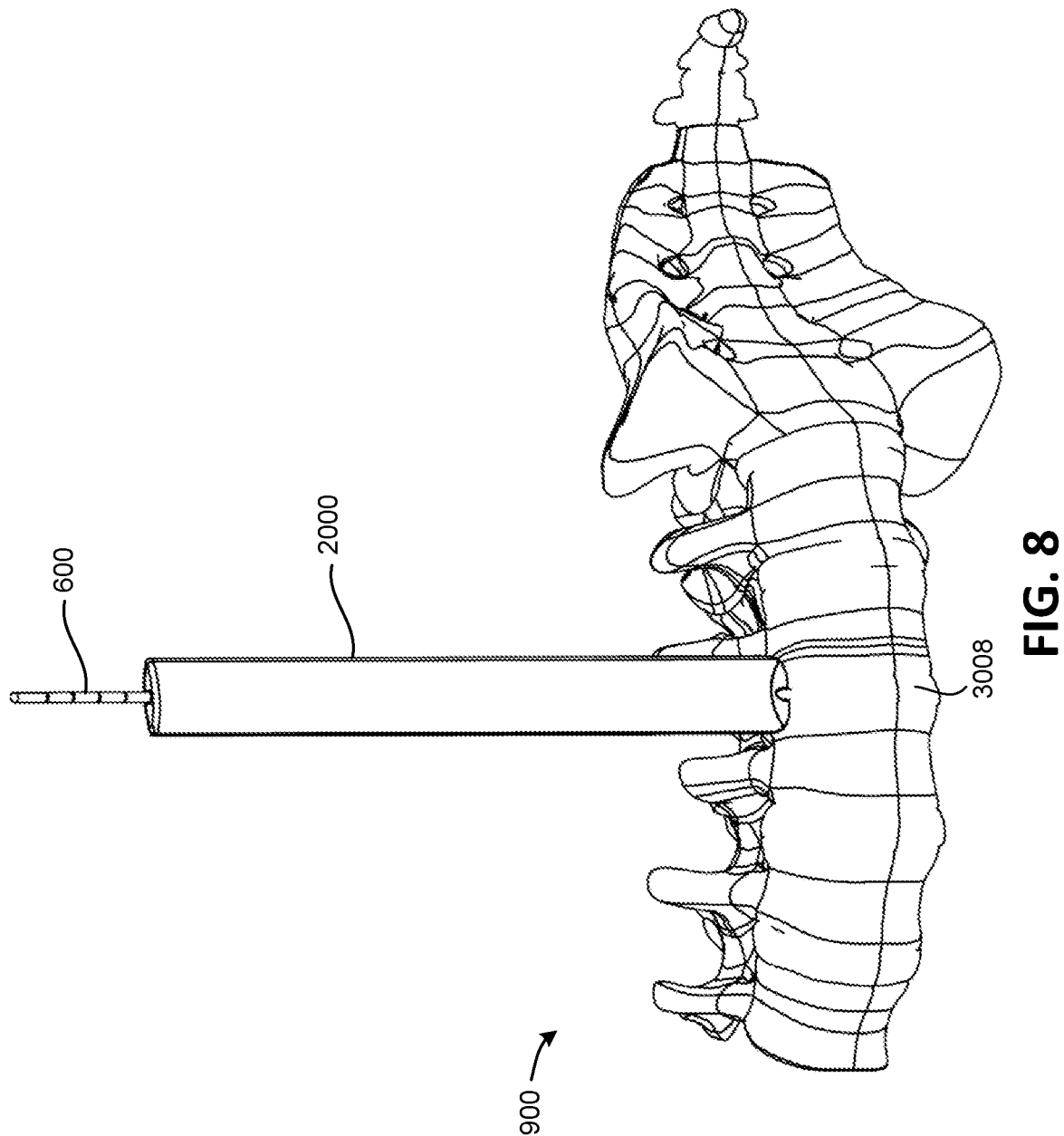
FIG. 8 is a perspective view of a third dilator inserted over the guidewire of FIG. 6.
Figure 9:
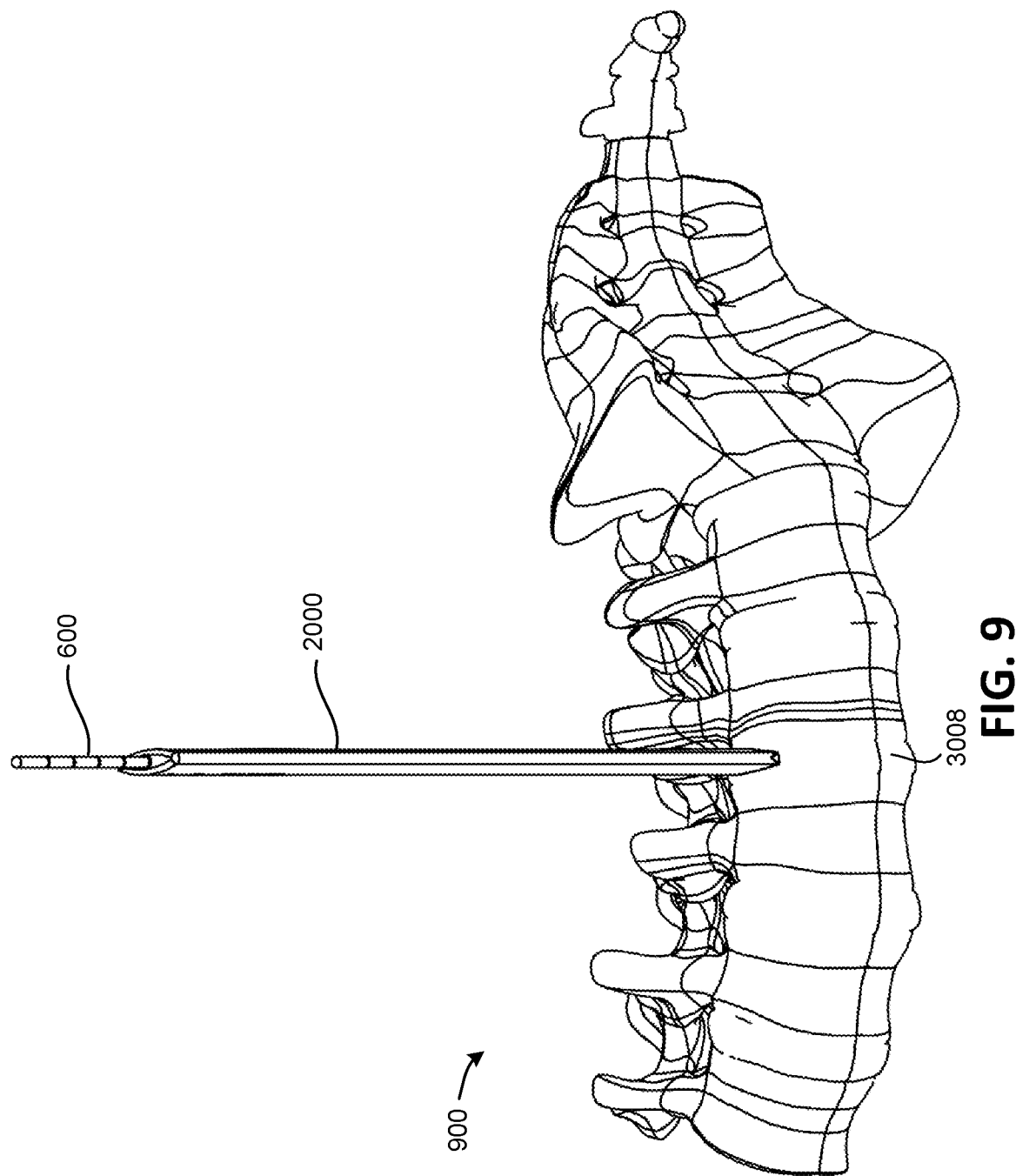
FIG. 9 is a perspective view of the third dilator of FIG. 8 rotated 90 degrees.

FIG. 8 is a perspective view of a third dilator 2000 inserted laterally proximate the target interbody space 3008 in a first orientation. The third dilator 2000 may be larger than the second dilator 1000 and may be inserted over the guide wire 600. FIG. 9 is a perspective view of the third dilator 2000 of FIG. 8 after it has been rotated 90 degrees in order to retract the psoas muscle, as previously discussed.

Figure 10:
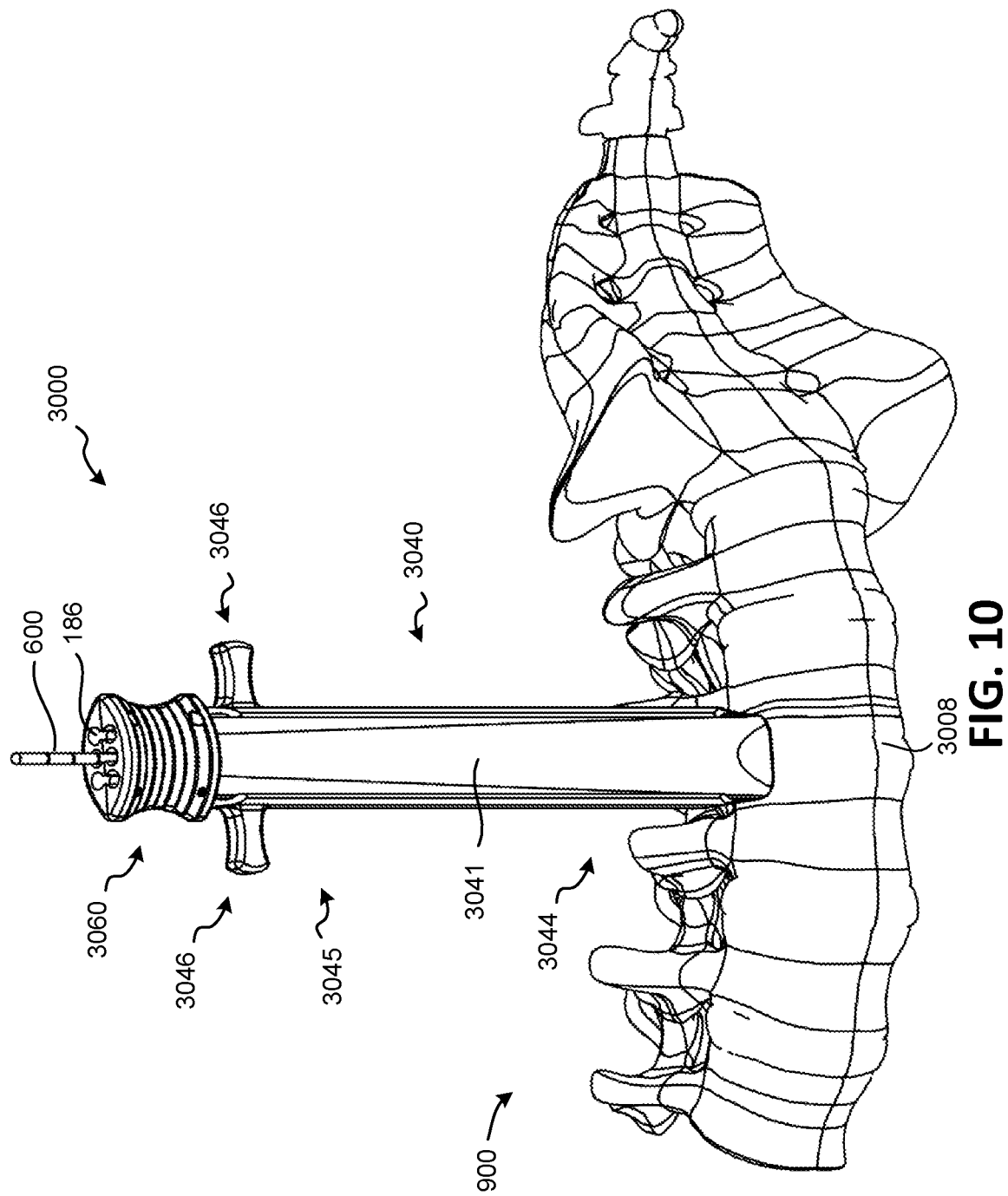
FIG. 10 is a perspective view of a guide dilator inserted over the guidewire of FIG. 6.
Figure 11:
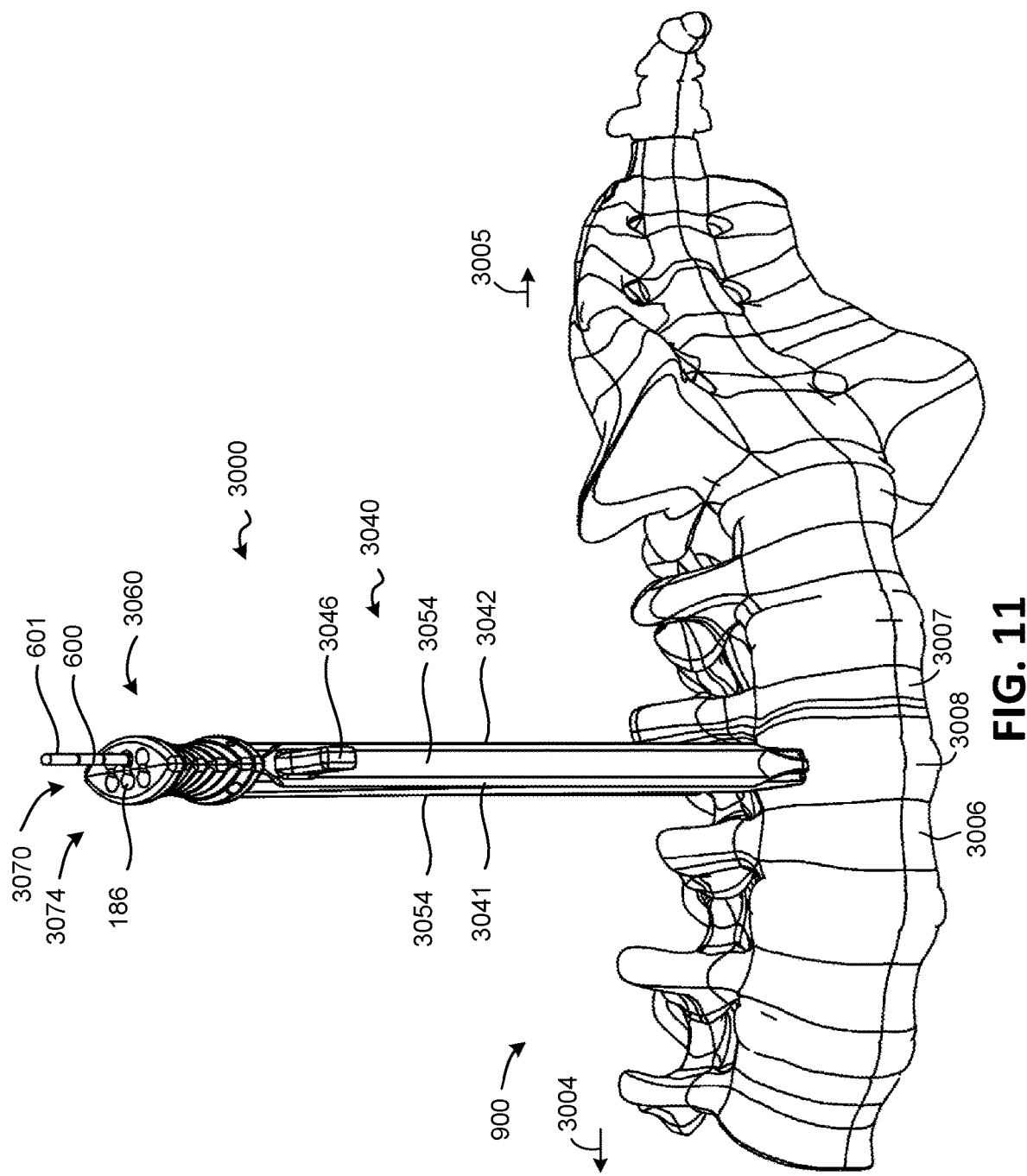
FIG. 11 is a perspective view of the guide dilator of FIG. 10 rotated 90 degrees.
Figure 12:
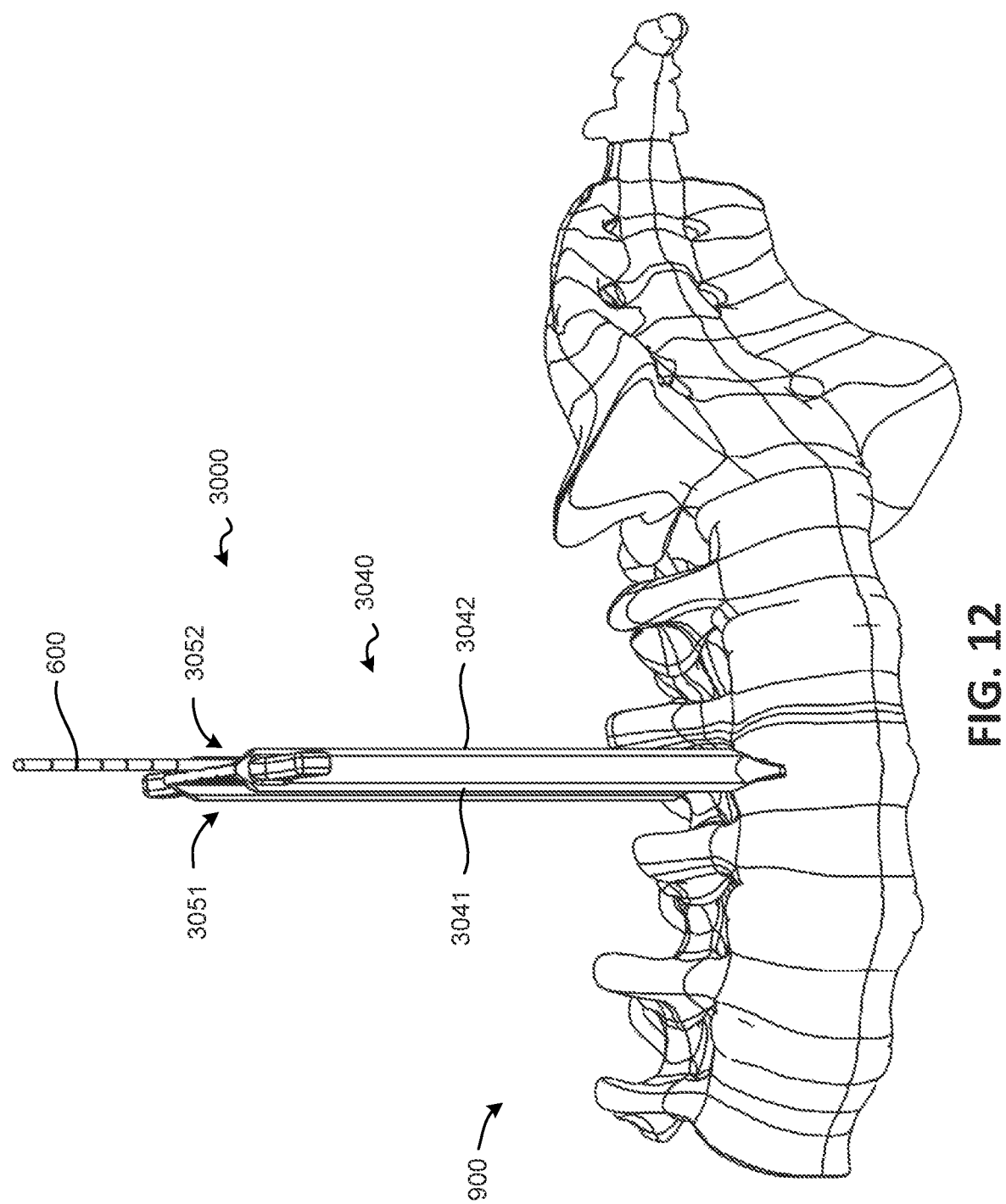
FIG. 12 is a perspective view of the guide dilator of FIG. 11 with an inner obturator removed.
Figure 13:
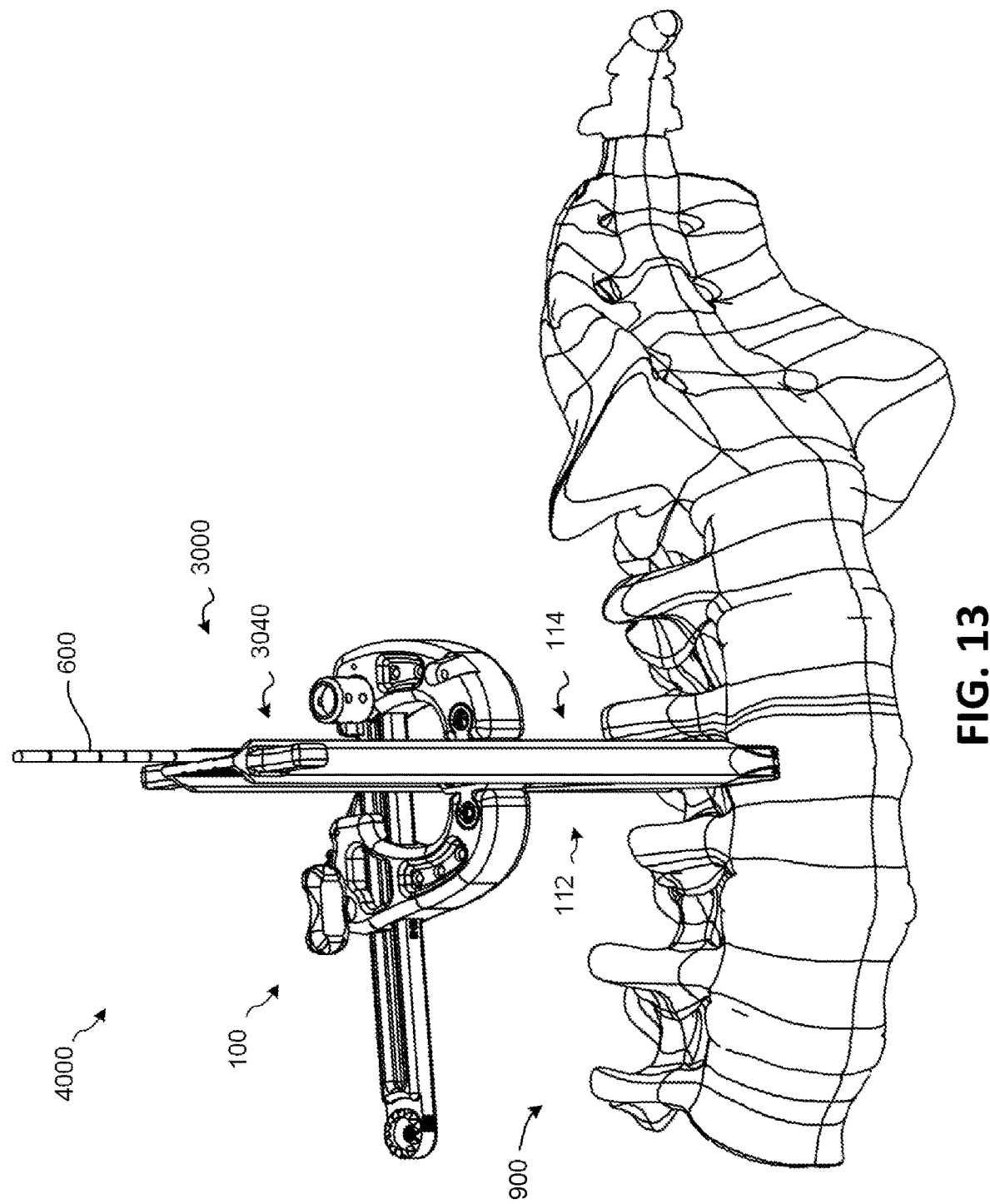
FIG. 13 is a perspective view of the guide dilator of FIG. 12 with the retractor system of FIG. 1A inserted into the guide dilator.
Figure 14:
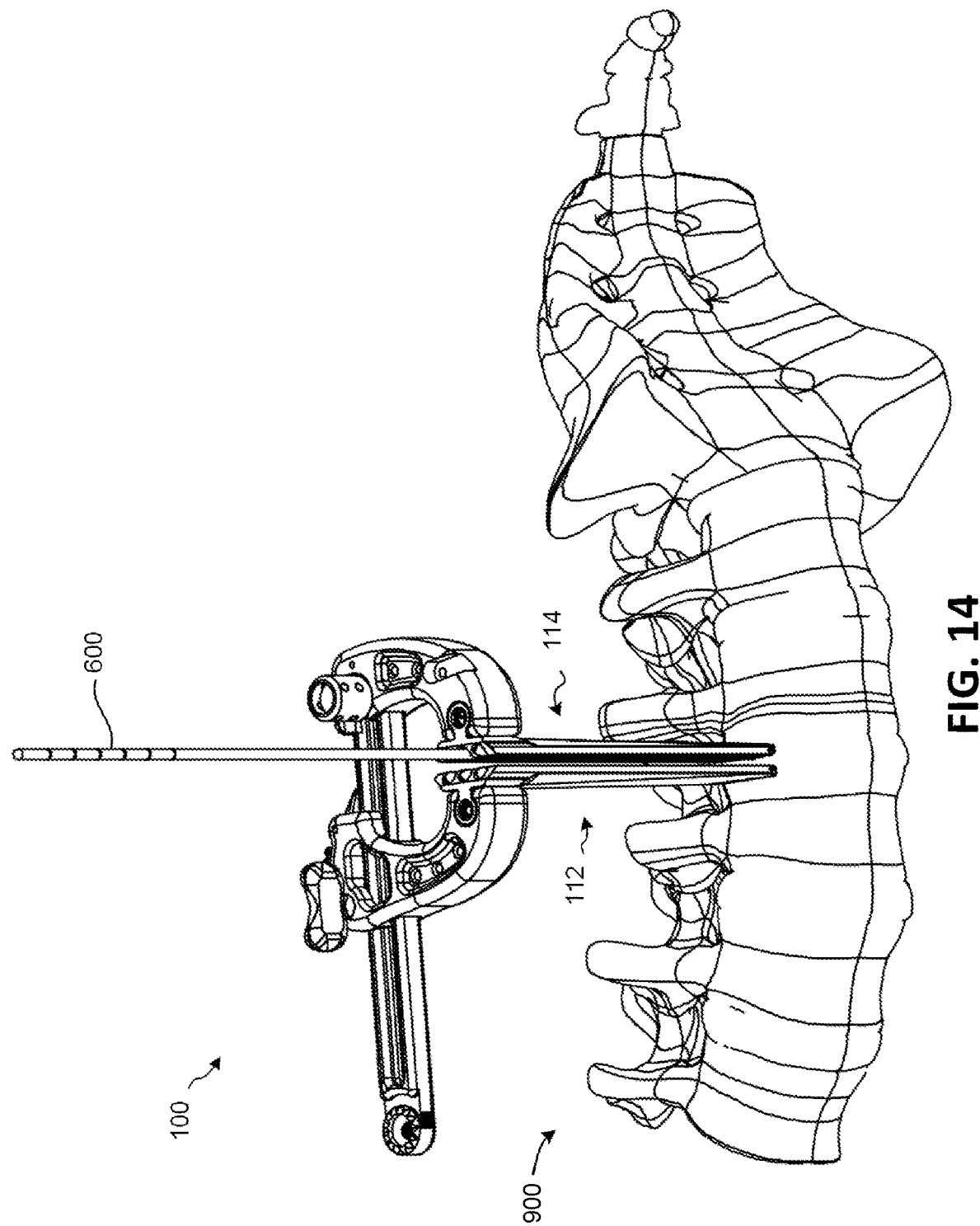
FIG. 14 is a perspective view of the retractor system of FIG. 13 with the guide dilator removed.

FIG. 10 is a perspective view of a guide dilator 3000 inserted laterally proximate the target interbody space 3008 in a first orientation. The guide dilator 3000 may be larger than the third dilator 2000 and may be inserted over the guide wire 600. FIG. 11 is a perspective view of the guide dilator 3000 of FIG. 10 after it has been rotated 90 degrees in order to retract the psoas muscle, as previously discussed. In this manner, the guide dilator 3000 may be utilized to spread tissues surrounding the access pathway proximate the interbody space 3008 and also dissect any psoas muscle from the surface of the interbody space. FIG. 12 is a perspective view of the guide dilator 3000 of FIG. 11 with an inner obturator 3060 of the guide dilator 3000 removed. FIG. 13 is a perspective view of the guide dilator 3000 of FIG. 12 with the retractor system 100 of FIG. 1A inserted into the guide dilator 3000 in place of the inner obturator 3060, which may together form a retractor system 4000 comprising the retractor system 100 in combination with the guide dilator 3000, according to another embodiment of the present disclosure. FIG. 14 is a perspective view of the retractor system 100 of FIG. 13 with a sheath 3040 of the guide dilator 3000 removed, leaving the retractor system 100 inserted proximate the spine.

As shown in FIGS. 10-13, the sheath 3040 of the guide dilator 3000 may retain the inner obturator 3060 therein. The sheath 3040 may have a proximal end 3045 and a distal end 3044, with handles 3046 extending outward from the proximal end 3045. The sheath 3040 may include a first side 3041 and a second side 3042, with walls 3054 that may define a first track or first slot 3051 and a second track or second slot 3052 that slidably receive the inner obturator 3060 within the sheath 3040. The first track or first slot 3051 and the second track or second slot 3052 may also be shaped to receive the first retractor blade 112 and the second retractor blade 114, respectively therein, as shown in FIG. 13.

The inner obturator 3060 may have a proximal end 3070 and a distal end (not visible), with a handle portion 3074 at the proximal end 3070 of the inner obturator 3060. The inner obturator 3060 may also include an interior surface (not visible in FIGS. 10-13) on which a number of grooves 186 (for example six) may be defined. Each of the grooves 186 may have a generally circular cross-sectional shape, which may define more than half of a circle. Thus, each of the grooves 186 may be capable of retaining a cylindrical member such as the guide wire 600.

The guide wire 600 may have a proximal end 601 and a distal end (not visible in FIGS. 10-13). The distal end of the guide wire 600 may include a sharpened tip, threaded tip, or other geometry designed to facilitate anchorage of the distal end in tissue at or near the surgical site. In some embodiments, the distal end of the guide wire 600 may be anchored in disc tissue (for example, the natural intervertebral disc) of the interbody space 3008. In alternative embodiments, the distal end of the guide wire 600 may be anchored in other tissue proximate the surgical site, such as in the first vertebral body 3006 or the second vertebral body 3007.

The spine 900 may have a cephalad end 3004 and a caudal end 3005 (see FIG. 11). An access pathway may be defined by providing access to an interbody space 3008 between a first vertebral body 3006 of the spine 900, and a second vertebral body 3007 of the spine 900. In some embodiments, the surgical procedure may include implantation of an interbody spacer (not shown) into the interbody space 3008 in order to facilitate bone in-growth and fusion between the first vertebral body 3006 and the second vertebral body 3007.

The guide dilator 3000 may be insertable into the access pathway to engage the tissue. As shown in FIGS. 12 and 13, the first side 3041 of the guide dilator 3000 may be shaped to be coupled to the first retractor blade 112 and the second side 3042 may be shaped to be coupled to the second retractor blade 114 to guide insertion of the first retractor blade 112 and the second retractor blade 114 into the access pathway.

In at least some embodiments, each of the first retractor blade 112, the second retractor blade 114, and the guide dilator 3000 may comprise grooves 186. The retractor system may also comprise a guide wire 600 receivable in the grooves 186 of the first retractor blade 112, the second retractor blade 114, and the guide dilator 3000. The guide wire 600 may comprise a distal end insertable into the surgical site along the access pathway. The retractor system may also include a first pin 201 (e.g., see FIG. 1D) receivable in the grooves 186 of the first retractor blade 112 and the second retractor blade 114. The first pin 201 may include a first distal end 211 anchorable in a first bone proximate the surgical site. The retractor system may further include a second pin 202 receivable in the grooves 186 of the first retractor blade 112 and the second retractor blade 114. The second pin 202 may also include a second distal end 212 anchorable in a second bone proximate the surgical site.

Once the retractor system 100 has been inserted proximate the spine 900 and the sheath 3040 of the guide dilator 3000 has been fully removed as shown in FIG. 14, the retractor system 100 may be retracted and secured into place, as will now be discussed with reference to FIGS. 15-20.

Figure 15:
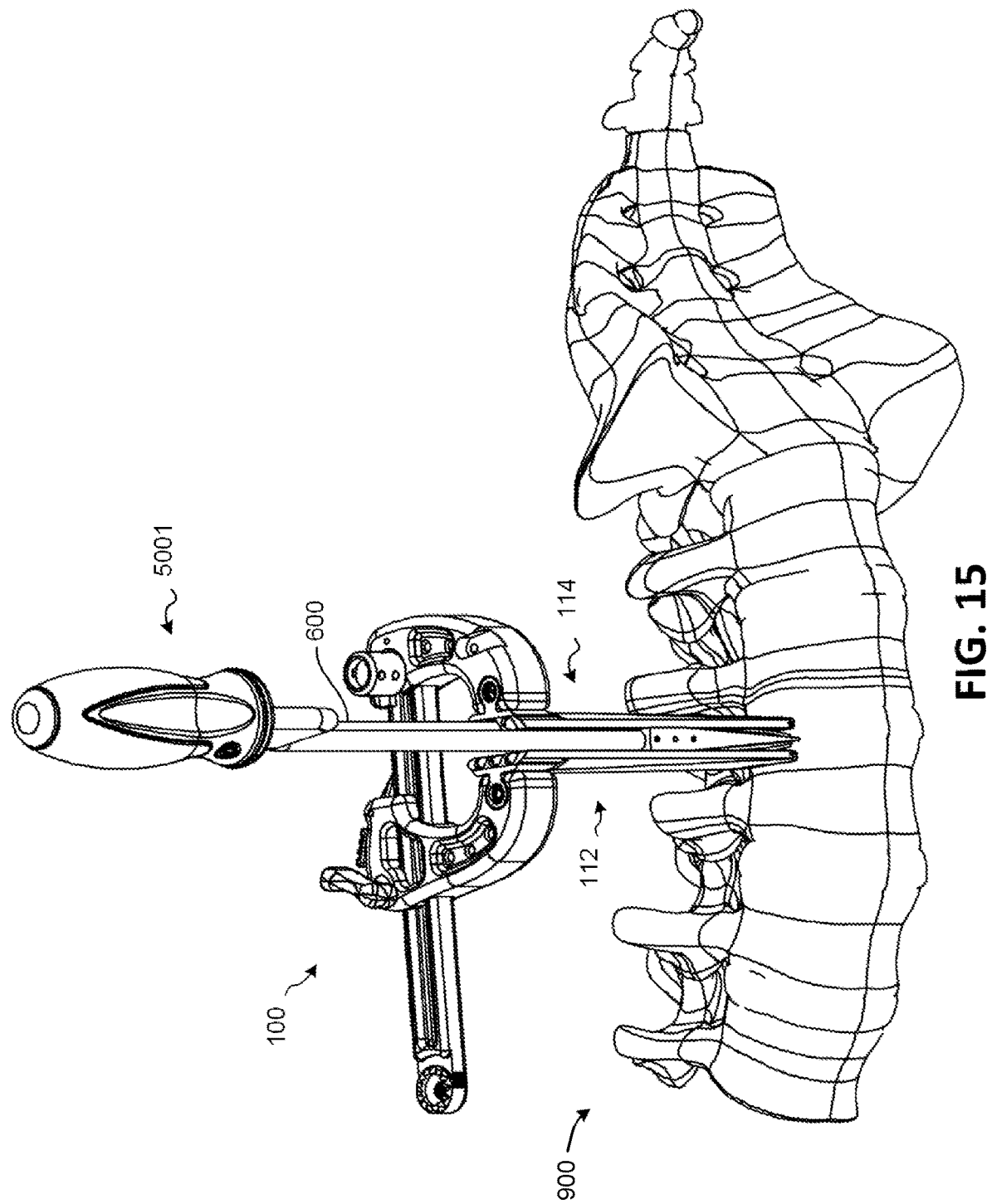
FIG. 15 is a perspective view of the retractor system of FIG. 14 with a first wedge distractor inserted between the blades of the retractor system.
Figure 16:
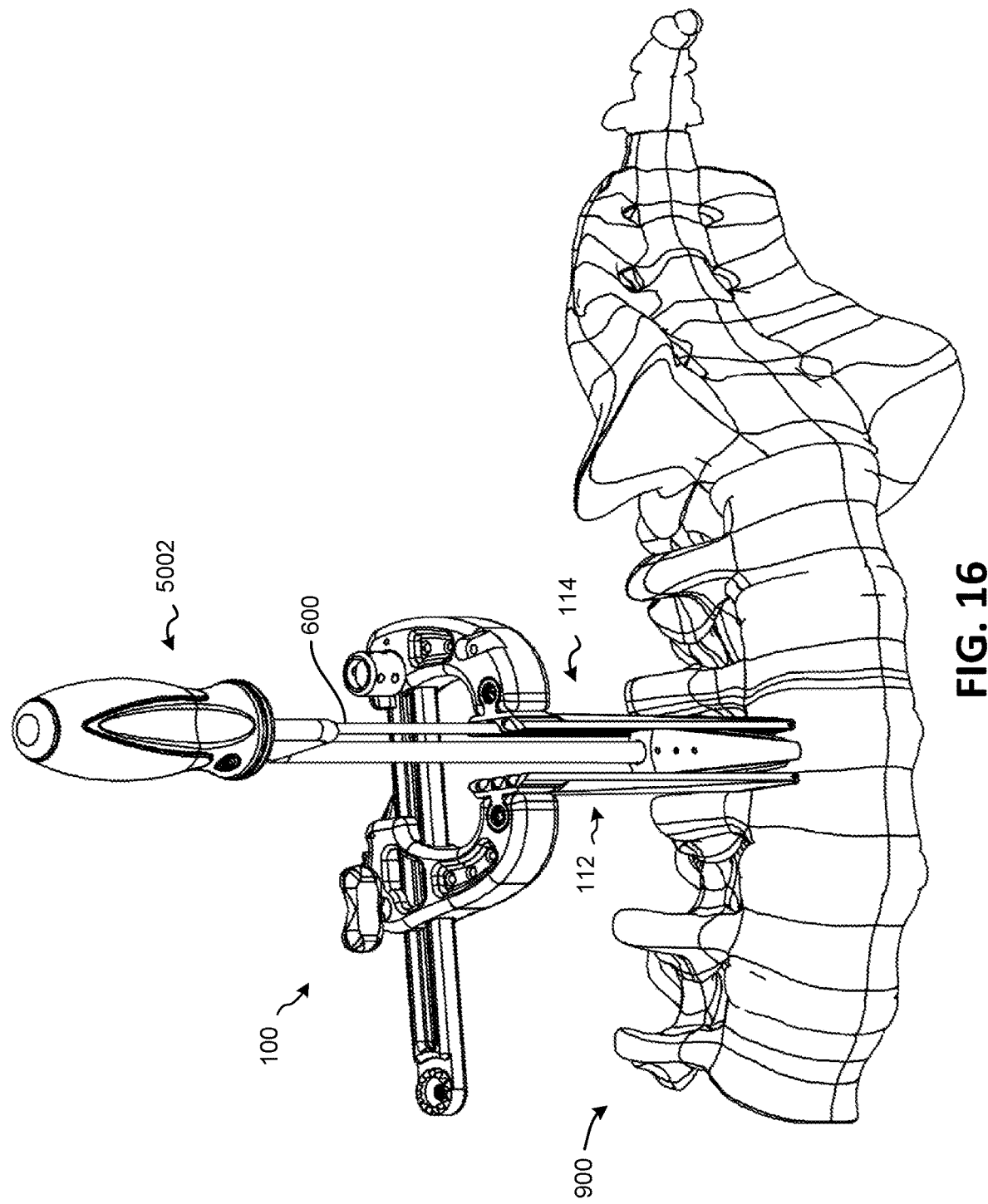
FIG. 16 is a perspective view of the retractor system of FIG. 15 with a second wedge distractor inserted between the blades of the retractor system.
Figure 17:
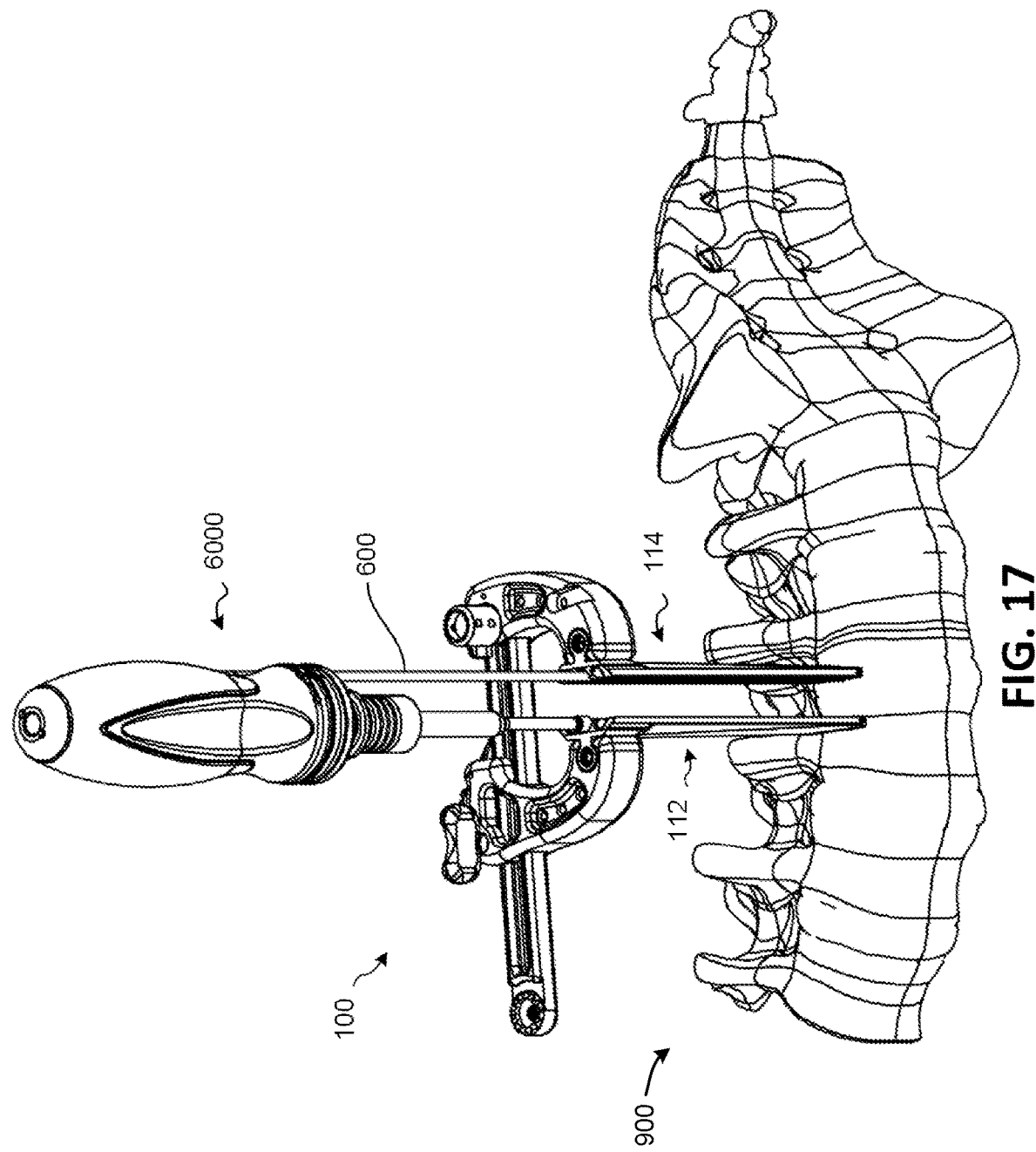
FIG. 17 is a perspective view of the retractor system of FIG. 16 showing a pin driver affixing a first pin into a first bone of the spine.
Figure 18:
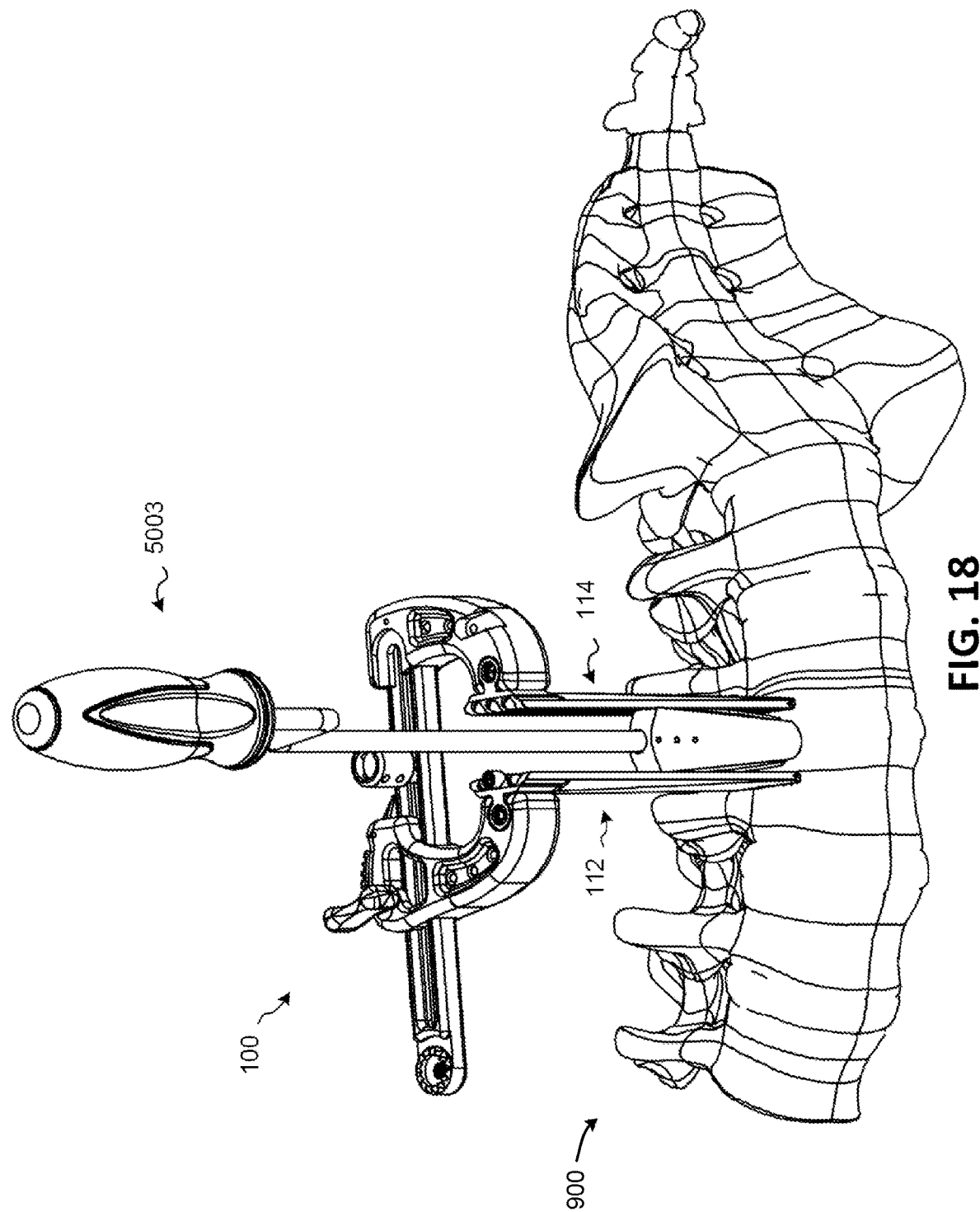
FIG. 18 is a perspective view of the retractor system of FIG. 17 with a third wedge distractor inserted between the blades of the retractor system.
Figure 19:
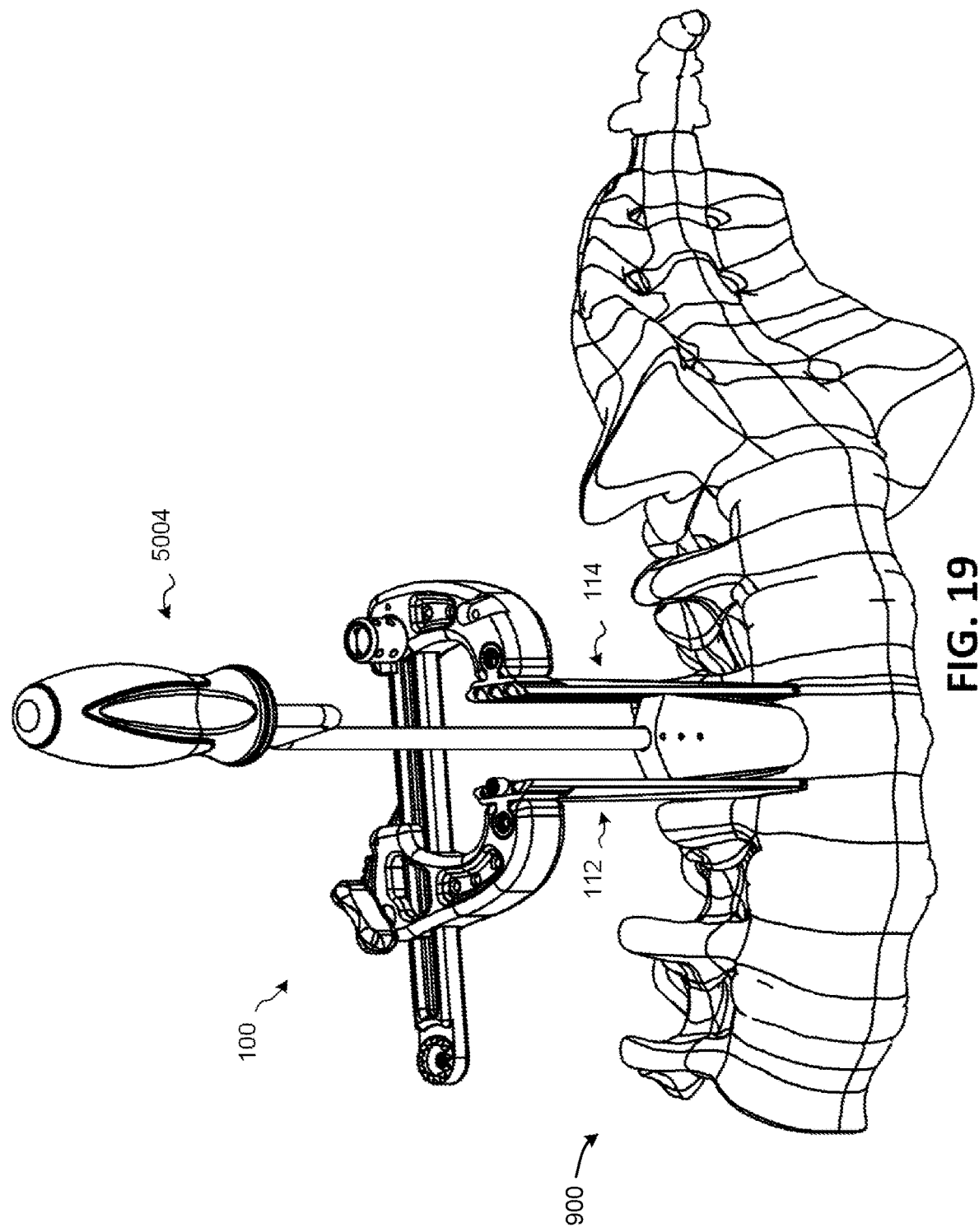
FIG. 19 is a perspective view of the retractor system of FIG. 18 with a fourth wedge distractor inserted between the blades of the retractor system.
Figure 20:
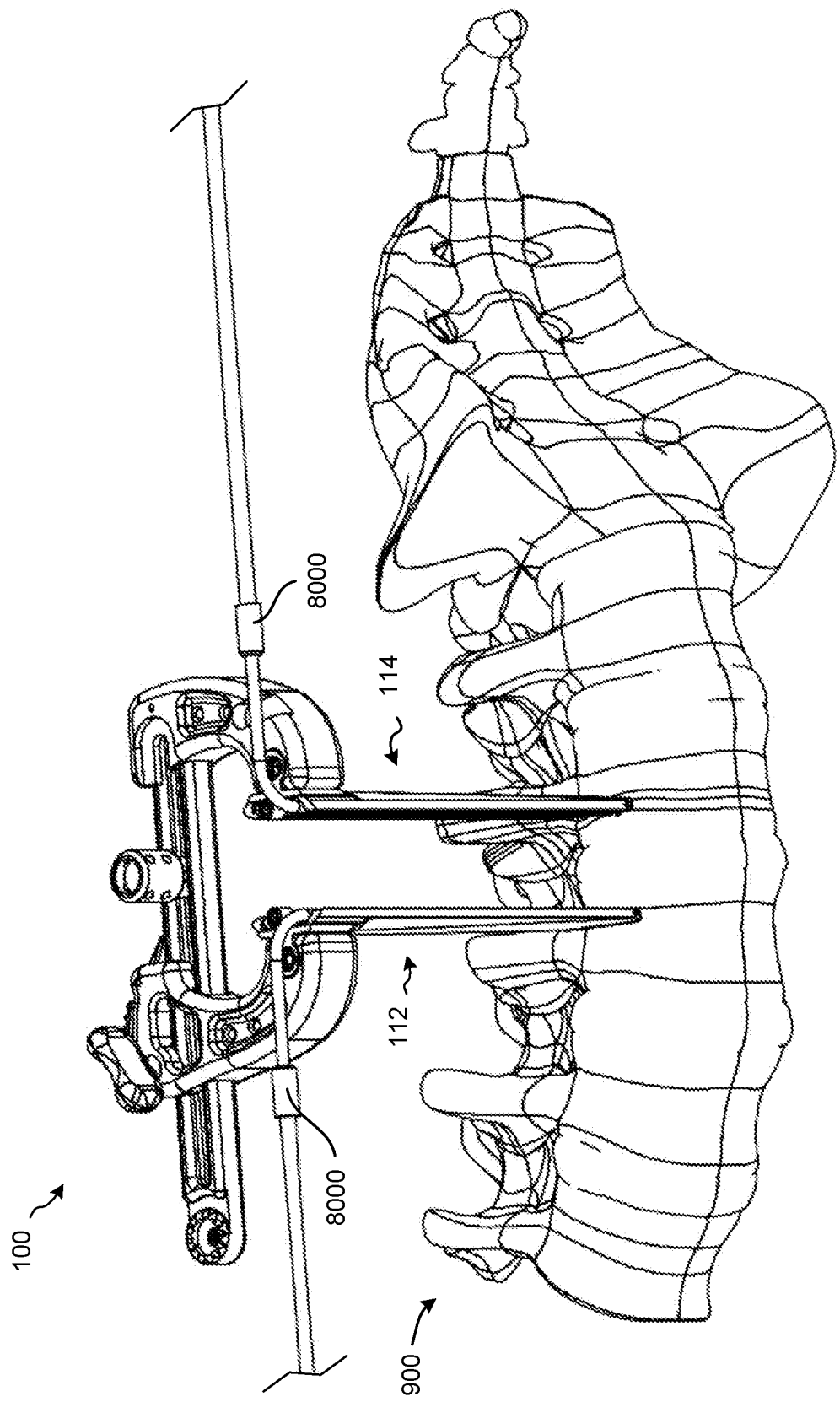
FIG. 20 is a perspective view of the retractor system of FIG. 19 after a second pin has been affixed into a second bone of the spine.

FIG. 15 is a perspective view of the retractor system 100 of FIG. 14 with a first wedge distractor 5001 inserted between the first and second retractor blades 112, 114 to push the first and second retractor blades 112, 114 apart from each other. FIG. 16 is a perspective view of the retractor system 100 of FIG. 15 with a larger second wedge distractor 5002 inserted between the first and second retractor blades 112, 114 to push the first and second retractor blades 112, 114 apart from each other even further. FIG. 17 is a perspective view of the retractor system 100 of FIG. 16 showing a pin driver 6000 affixing a first pin (not visible in FIG. 17) into a first bone of the spine 900. FIG. 18 is a perspective view of the retractor system 100 of FIG. 17 with yet a larger third wedge distractor 5003 inserted between the first and second retractor blades 112, 114 to push the first and second retractor blades 112, 114 apart from each other even further. FIG. 19 is a perspective view of the retractor system 100 of FIG. 17 with yet a larger fourth wedge distractor 5004 inserted between the first and second retractor blades 112, 114 to push the first and second retractor blades 112, 114 apart from each other even further. FIG. 20 is a perspective view of the retractor system 100 of FIG. 19 after a second pin (not visible in FIG. 20) has been affixed into a second bone of the spine to secure the retractor system 100 in place. FIG. 20 also illustrates one or more light sources 8000 that may be utilized to visually aid the surgeon. Each of the one or more light sources 8000 may be sized and shaped to fit within the grooves 186 formed in the first and second retractor blades 112, 114. The retractor system 100 of FIG. 20 may be further modified with additional components in order to achieve additional retraction capabilities and/or additional fixation, as will now be discussed with reference to FIGS. 21-24.

Figure 21:
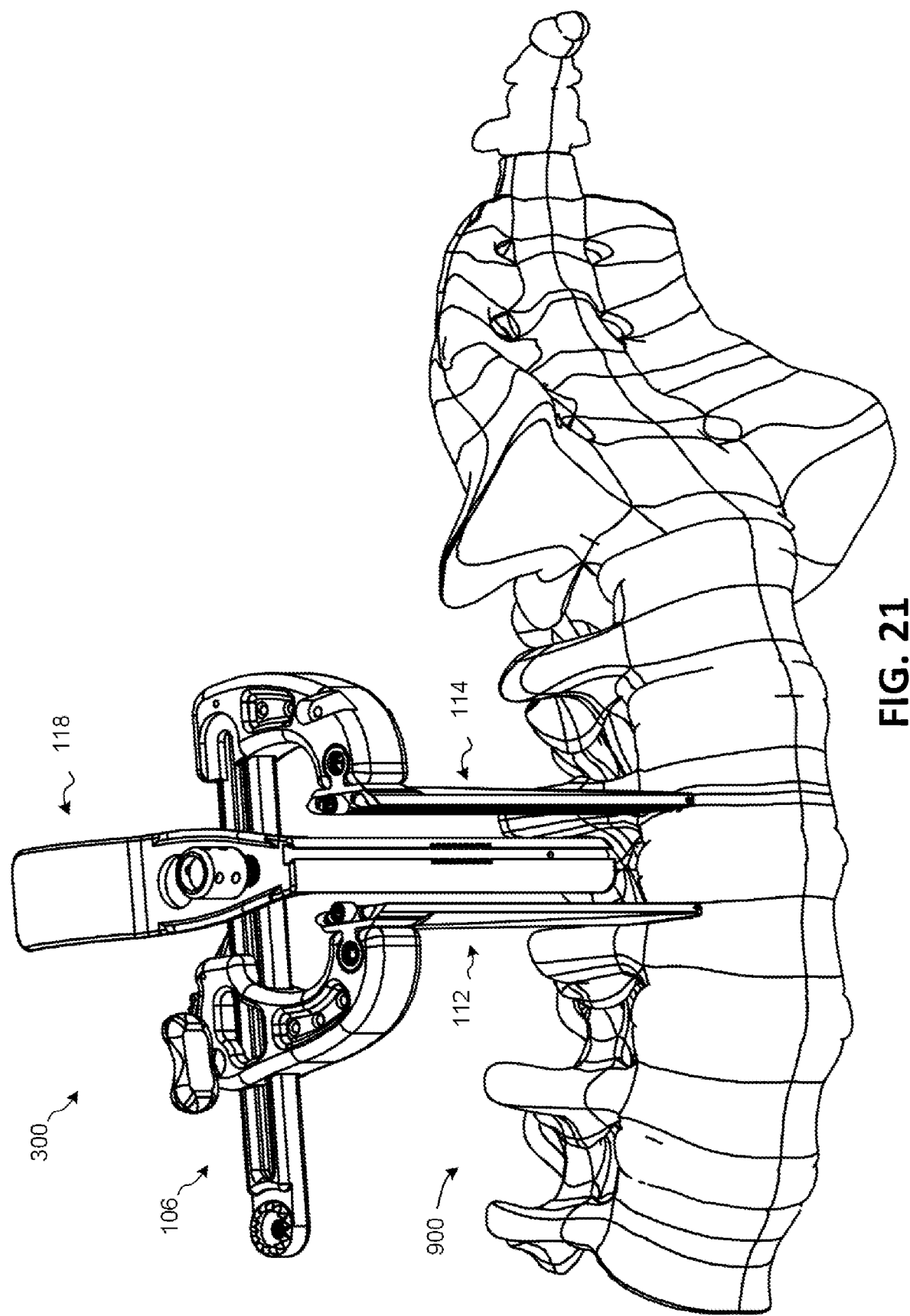
FIG. 21 is a perspective view of the retractor system of FIG. 1D inserted proximate a spine, according to one embodiment of the present disclosure.

FIG. 21 is a perspective view of the retractor system 100 of FIG. 20 with an additional or fourth retractor blade 118 coupled to the rack 106 in order to form the retractor system 300 previously discussed with reference to FIG. 1D. In this manner the fourth retractor blade 118 may provide additional retraction of soft tissues posteriorly.

Figure 22:
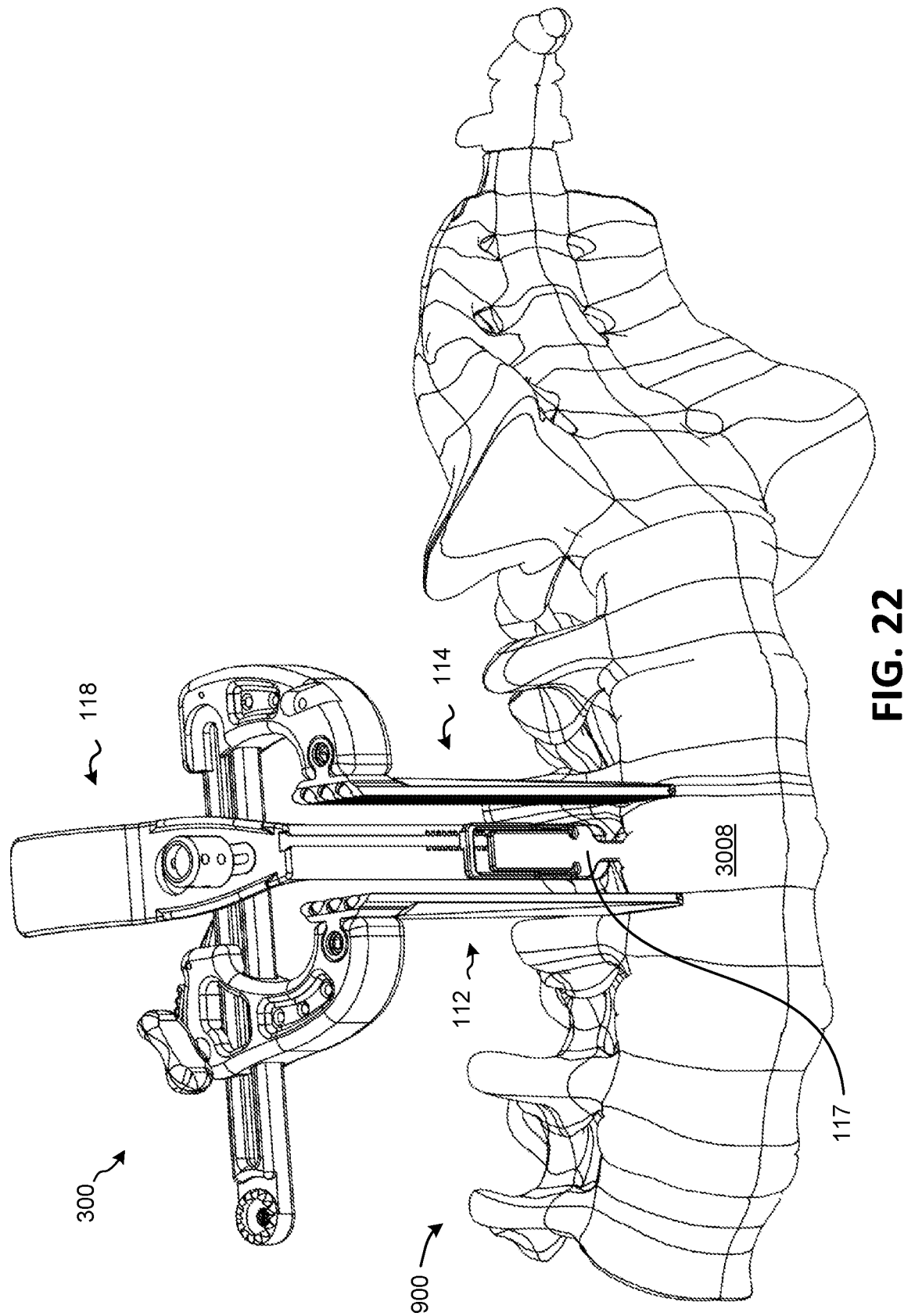
FIG. 22 is a perspective view of the retractor system of FIG. 21 showing the disc shim tool of FIG. 3B attaching a disc shim to a blade of the retractor system.

FIG. 22 is a perspective view of the retractor system 300 of FIG. 21 showing a disc shim 117 coupled to the fourth retractor blade 118, as previously discussed. In this manner, the disc shim 117 may provide extra fixation for the fourth retractor blade 118 when the disc shim 117 is wedged into the interbody space 3008.

Figure 23:
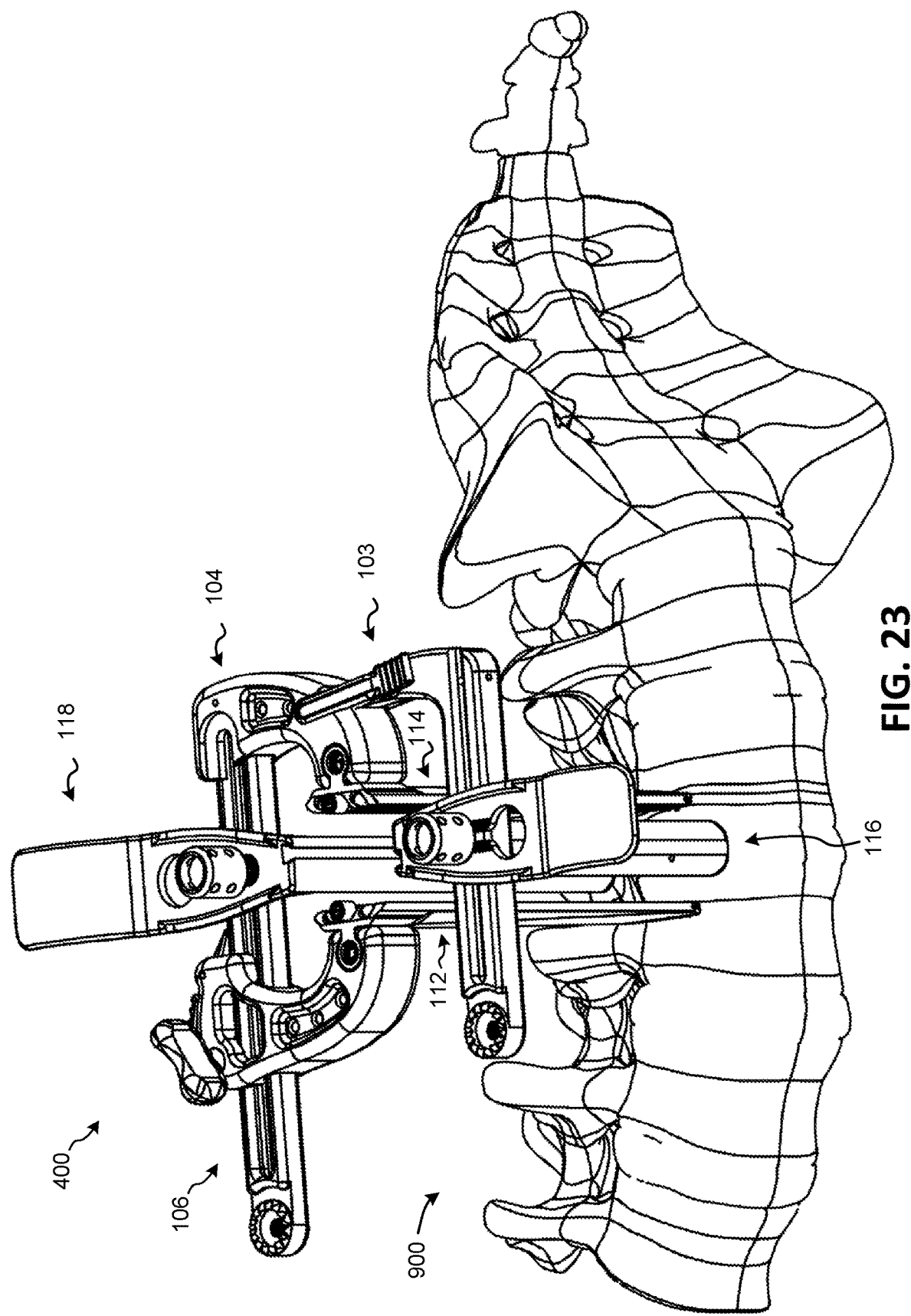
FIG. 23 is a perspective view of the retractor system of FIG. 1C inserted proximate a spine, according to one embodiment of the present disclosure.

FIG. 23 is a perspective view of the retractor system 300 of FIG. 22 with an additional or third retractor blade 116 coupled to the third arm 103. The third arm 103 may also be coupled to the second arm 104 in order to form the retractor system 400 previously discussed with reference to FIG. 1C. In this manner the third retractor blade 116 may provide additional retraction of soft tissues anteriorly.

Figure 24:
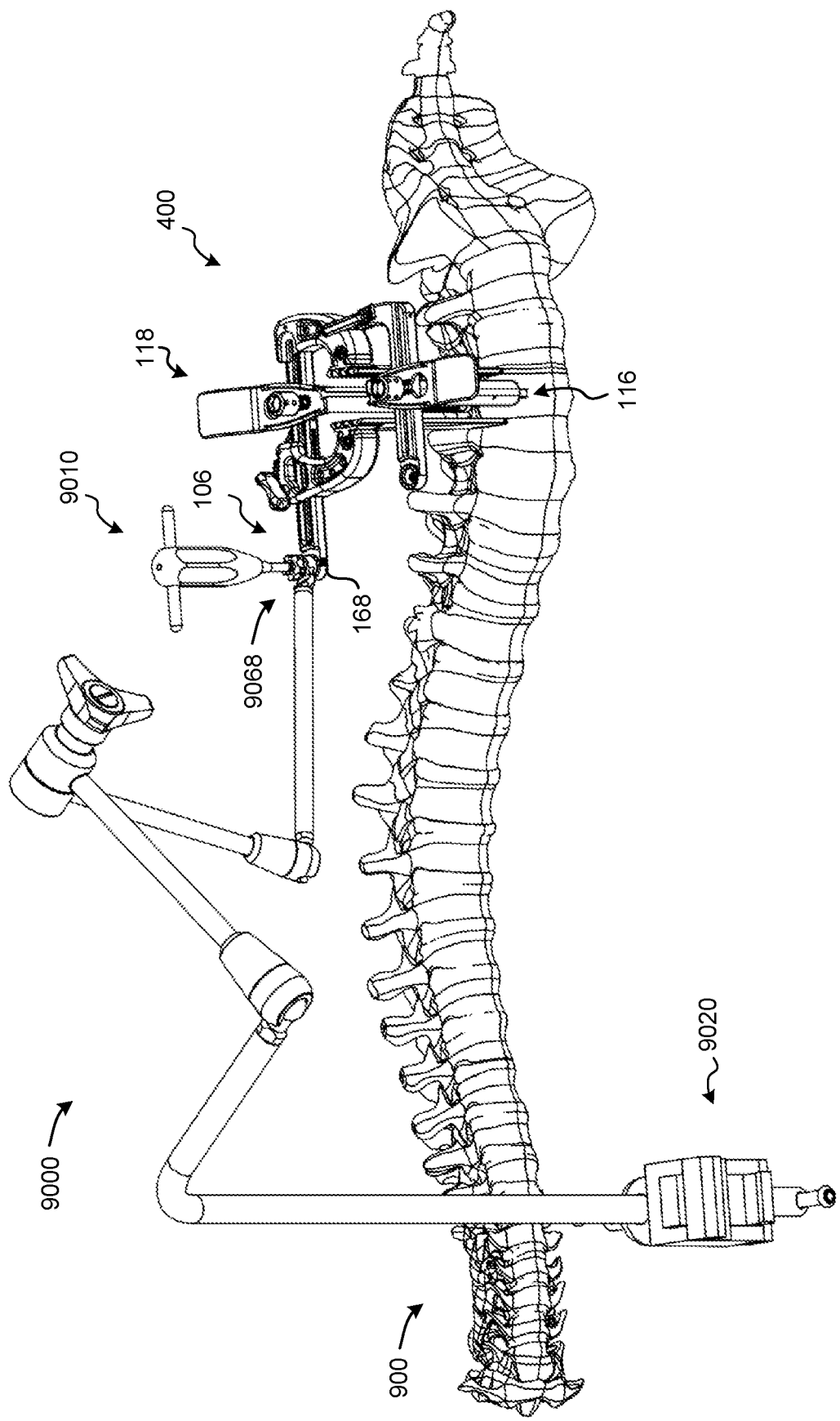
FIG. 24 is a perspective view of the retractor system of FIG. 23 fixedly mounted to an attachment arm proximate the surgical site, according to one embodiment of the present disclosure.

FIG. 24 is a perspective view of the retractor system 400 of FIG. 23 fixedly mounted to an attachment arm 9000 proximate the surgical site, as previously discussed. The mounting feature 168 of the rack 106 may be fixedly mounted to the attachment arm 9000 via a corresponding mounting feature 9068 of the attachment arm 9000 which may include a bolt, boss, or other protrusion (not shown) that may extend through the hole of the mounting feature 168. A driver tool 9010 may also be utilized to secure the mounting features 168, 9068 together. In this manner, additional stability and/or fixation of the retractor system 400 relative to the spine 900 of the patient may be achieved.

It will be understood that any of the retractor systems, components, and/or methods described herein may be mixed and matched in any number of combinations without departing from the spirit or scope of the present disclosure. For example, the attachment arm 9000 of FIG. 24 may be utilized with any of the retractor systems, components, and/or methods described herein, etc.

Any methods disclosed herein comprise one or more steps or actions for performing the described method. One or more of the method steps and/or actions may be omitted from and of the methods disclosed herein. Moreover, any of the method steps and/or actions may be interchanged with one another. In other words, unless a specific order of steps or actions is required for proper operation of the embodiment, the order and/or use of specific steps and/or actions may be modified.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

As defined herein, "substantially equal to" means "equal to," or within about a + or −10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the systems, methods, and devices disclosed herein.

What is claimed is:

1. A retractor system configured to provide access to a surgical site along an access pathway surrounded by tissue, the retractor system comprising:
a first arm;
a second arm connectable to the first arm via a rack such that the first arm is translatable along the rack in a first retraction direction relative to the second arm, the second arm comprising a connection interface;
a first retractor blade securable to the first arm such that the first retractor blade extends into the access pathway, the first retractor blade comprising a first tissue engagement surface that engages the tissue;
a second retractor blade securable to the second arm such that the second retractor blade extends into the access pathway, the second retractor blade comprising a second tissue engagement surface that engages the tissue;
a third arm comprising a connection feature removably securable to the connection interface of the second arm to removably secure the third arm to an intermediate portion of the second arm; and
a third retractor blade securable to the third arm such that the third retractor blade extends into the access pathway to engage the tissue, the third retractor blade comprising a third tissue engagement surface that engages the tissue, the third retractor blade comprising a third cross-sectional shape oriented generally parallel to the first retraction direction;
wherein:
the connection interface comprises a first recess and a second recess formed in the intermediate portion of the second arm; and
the connection feature comprises an actuator arm and a lower arm, wherein the actuator arm is receivable within the first recess and the lower arm is receivable within the second recess to removably secure the third arm to the intermediate portion of the second arm.

2. The retractor system of claim 1, wherein at least one of the second arm and the third arm comprises a locking mechanism comprising an actuator that can be actuated to move the locking mechanism between:
a locked configuration in which the connection feature is locked in place relative to the connection interface; and
an unlocked configuration in which the connection feature is removable from the connection interface.

3. The retractor system of claim 1, wherein:
the first arm comprises a first blade interface;
the first retractor blade comprises a first arm interface securable to the first blade interface;
one of the first blade interface and the first arm interface comprises a socket defined by a partial wall defining a circumferential opening; and
the other of the first blade interface and the first arm interface comprises a boss at one end of a bridge, wherein the boss is insertable into the socket such that the bridge resides in the circumferential opening.

4. The retractor system of claim 3, wherein:
the first blade interface comprises the socket and the first arm interface comprises the boss and the bridge; and
the boss is insertable into the socket along an insertion direction that is generally parallel to the access pathway.

5. The retractor system of claim 1, further comprising a guide dilator insertable into the access pathway to engage the tissue, the guide dilator comprising a first side shaped to be coupled to the first retractor blade and a second side shaped to be coupled to the second retractor blade to guide insertion of the first retractor blade and the second retractor blade into the access pathway.

6. The retractor system of claim 5, wherein:
the first side comprises a first slot shaped to receive the first retractor blade; and
the second side comprises a second slot shaped to receive the second retractor blade.

7. The retractor system of claim 6, wherein:
each of the first retractor blade and the second retractor blade comprises a groove; and
the retractor system further comprises:
a guide wire receivable in the grooves of the first retractor blade and the second retractor blade, the guide wire comprising a distal end insertable into the surgical site along the access pathway;
a first pin receivable in the grooves of the first retractor blade and the second retractor blade, the first pin comprising a first distal end anchorable in a first bone proximate the surgical site; and
a second pin receivable in the grooves of the first retractor blade and the second retractor blade, the second pin comprising a second distal end anchorable in a second bone proximate the surgical site.

8. The retractor system of claim 1, wherein:
the first arm is slidably coupled to the rack to provide translation of the first arm relative to the second arm along the rack in the first retraction direction; and
the retractor system further comprises a fourth retractor blade securable to the rack such that the fourth retractor blade extends into the access pathway to engage the tissue, the fourth retractor blade comprising a fourth tissue engagement surface that engages the tissue, the fourth retractor blade comprising a fourth cross-sectional shape oriented generally parallel to the first retraction direction;
wherein, with the first retractor blade secured to the first arm, the second retractor blade secured to the second arm, the third retractor blade secured to the third arm, and the fourth retractor blade secured to the rack:
the second retractor blade is generally parallel to the first retractor blade; and
the fourth retractor blade is generally parallel to the third retractor blade and perpendicular to the first and second retractor blades.

9. The retractor system of claim 1, wherein the rack coupled to the first arm and the second arm comprises a mounting feature securable to an attachment arm fixedly mounted proximate the surgical site.

10. A retractor system configured to provide access to a surgical site along an access pathway surrounded by tissue, the retractor system comprising:
- a first arm;
- a second arm connectable to the first arm via a rack such that the first arm is translatable along the rack in a first retraction direction relative to the second arm, the second arm comprising a connection interface;
- a first retractor blade securable to the first arm such that the first retractor blade extends into the access pathway, the first retractor blade comprising a first tissue engagement surface that engages the tissue;
- a second retractor blade securable to the second arm such that the second retractor blade extends into the access pathway, the second retractor blade comprising a second tissue engagement surface that engages the tissue;
- a third arm comprising a connection feature removably securable to the connection interface; and
- a third retractor blade securable to the third arm such that the third retractor blade extends into the access pathway to engage the tissue, the third retractor blade comprising a third tissue engagement surface that engages the tissue, the third retractor blade comprising a third cross-sectional shape oriented generally parallel to the first retraction direction, wherein the first arm is slidably coupled to the rack to provide translation of the first arm relative to the second arm along the rack in the first retraction direction; and
- a fourth retractor blade securable to the rack such that the fourth retractor blade extends into the access pathway to engage the tissue, the fourth retractor blade comprising a fourth tissue engagement surface that engages the tissue, the fourth retractor blade comprising a fourth cross-sectional shape oriented generally parallel to the first retraction direction;

wherein:
- the first arm comprises a first blade interface;
- the first retractor blade comprises a first arm interface securable to the first blade interface;
- the first arm interface is engageable with the first blade interface by moving the first arm interface, relative to the first blade interface, along an insertion direction generally parallel to the access pathway and toward the surgical site; and
- with the first retractor blade secured to the first arm, the second retractor blade secured to the second arm, the third retractor blade secured to the third arm, and the fourth retractor blade secured to the rack:
  - the second retractor blade is generally parallel to the first retractor blade; and
  - the fourth retractor blade is generally parallel to the third retractor blade and perpendicular to the first and second retractor blades.

11. The retractor system of claim 10, wherein:
one of the first blade interface and the first arm interface comprises a socket defined by a partial wall defining a circumferential opening; and
the other of the first blade interface and the first arm interface comprises a boss at one end of a bridge, wherein the boss is insertable into the socket such that the bridge resides in the circumferential opening.

12. The retractor system of claim 11, wherein:
the first blade interface comprises the socket and the first arm interface comprises the boss and the bridge; and
the boss is insertable into the socket along the insertion direction.

13. The retractor system of claim 11, wherein:
the socket comprises a socket hole;
the boss comprises a boss hole; and
the retractor system further comprises a fastener insertable into the boss hole and the socket hole along the insertion direction to secure the boss within the socket.

14. A retractor system configured to provide access to a surgical site along an access pathway surrounded by tissue, the retractor system comprising:
- a first arm;
- a second arm connectable to the first arm via a rack such that the first arm is translatable along the rack in a first retraction direction relative to the second arm, the second arm comprising a connection interface;
- a first retractor blade securable to the first arm such that the first retractor blade extends into the access pathway, the first retractor blade comprising a first tissue engagement surface that engages the tissue;
- a second retractor blade securable to the second arm such that the second retractor blade extends into the access pathway, the second retractor blade comprising a second tissue engagement surface that engages the tissue;
- a third arm comprising a connection feature removably securable to the connection interface of the second arm to removably secure the third arm to an intermediate portion of the second arm; and
- a third retractor blade securable to the third arm such that the third retractor blade extends into the access pathway to engage the tissue, the third retractor blade comprising a third tissue engagement surface that engages the tissue, the third retractor blade comprising a third cross-sectional shape oriented generally parallel to the first retraction direction; and
- a guide dilator insertable into the access pathway to engage the tissue, the guide dilator comprising a first side shaped to be coupled to the first retractor blade and a second side shaped to be coupled to the second retractor blade to guide insertion of the first retractor blade and the second retractor blade into the access pathway;

wherein:
- the first side comprises a first slot shaped to receive the first retractor blade;
- the second side comprises a second slot shaped to receive the second retractor blade;
- each of the first retractor blade and the second retractor blade comprises a groove; and
- the retractor system further comprises:
  - a guide wire receivable in the grooves of the first retractor blade and the second retractor blade, the guide wire comprising a distal end insertable into the surgical site along the access pathway;
  - a first pin receivable in the grooves of the first retractor blade and the second retractor blade, the first pin comprising a first distal end anchorable in a first bone proximate the surgical site; and
  - a second pin receivable in the grooves of the first retractor blade and the second retractor blade, the second pin comprising a second distal end anchorable in a second bone proximate the surgical site.

15. The retractor system of claim 14, wherein at least one of the second arm and the third arm comprises a locking mechanism comprising an actuator that can be actuated to move the locking mechanism between:
- a locked configuration in which the connection feature is locked in place relative to the connection interface; and
- an unlocked configuration in which the connection feature is removable from the connection interface.

16. The retractor system of claim 14, wherein:
the connection interface comprises a first recess and a second recess formed in the intermediate portion of the second arm; and
the connection feature comprises an actuator arm and a lower arm, wherein the actuator arm is receivable within the first recess and the lower arm is receivable within the second recess to removably secure the third arm to the intermediate portion of the second arm.

17. The retractor system of claim 14, wherein:
the first arm comprises a first blade interface;
the first retractor blade comprises a first arm interface securable to the first blade interface;
one of the first blade interface and the first arm interface comprises a socket defined by a partial wall defining a circumferential opening;
the other of the first blade interface and the first arm interface comprises a boss at one end of a bridge, wherein the boss is insertable into the socket such that the bridge resides in the circumferential opening;
the first blade interface comprises the socket and the first arm interface comprises the boss and the bridge; and
the boss is insertable into the socket along an insertion direction that is generally parallel to the access pathway.

18. A retractor system configured to provide access to a surgical site along an access pathway surrounded by tissue, the retractor system comprising:
a first arm;
a second arm connectable to the first arm via a rack such that the first arm is translatable along the rack in a first retraction direction relative to the second arm, the second arm comprising a connection interface;
a first retractor blade securable to the first arm such that the first retractor blade extends into the access pathway, the first retractor blade comprising a first tissue engagement surface that engages the tissue;
a second retractor blade securable to the second arm such that the second retractor blade extends into the access pathway, the second retractor blade comprising a second tissue engagement surface that engages the tissue;
a third arm comprising a connection feature removably securable to the connection interface of the second arm to removably secure the third arm to an intermediate portion of the second arm; and
a third retractor blade securable to the third arm such that the third retractor blade extends into the access pathway to engage the tissue, the third retractor blade comprising a third tissue engagement surface that engages the tissue, the third retractor blade comprising a third cross-sectional shape oriented generally parallel to the first retraction direction;
wherein:
the first arm is slidably coupled to the rack to provide translation of the first arm relative to the second arm along the rack in the first retraction direction; and
the retractor system further comprises a fourth retractor blade securable to the rack such that the fourth retractor blade extends into the access pathway to engage the tissue, the fourth retractor blade comprising a fourth tissue engagement surface that engages the tissue, the fourth retractor blade comprising a fourth cross-sectional shape oriented generally parallel to the first retraction direction;
with the first retractor blade secured to the first arm, the second retractor blade secured to the second arm, the third retractor blade secured to the third arm, and the fourth retractor blade secured to the rack:
the second retractor blade is generally parallel to the first retractor blade; and
the fourth retractor blade is generally parallel to the third retractor blade and perpendicular to the first and second retractor blades.

19. The retractor system of claim 18, wherein at least one of the second arm and the third arm comprises a locking mechanism comprising an actuator that can be actuated to move the locking mechanism between:
a locked configuration in which the connection feature is locked in place relative to the connection interface; and
an unlocked configuration in which the connection feature is removable from the connection interface.

20. The retractor system of claim 18, wherein:
the connection interface comprises a first recess and a second recess formed in the intermediate portion of the second arm; and
the connection feature comprises an actuator arm and a lower arm, wherein the actuator arm is receivable within the first recess and the lower arm is receivable within the second recess to removably secure the third arm to the intermediate portion of the second arm.

21. The retractor system of claim 18, wherein:
the first arm comprises a first blade interface;
the first retractor blade comprises a first arm interface securable to the first blade interface;
one of the first blade interface and the first arm interface comprises a socket defined by a partial wall defining a circumferential opening;
the other of the first blade interface and the first arm interface comprises a boss at one end of a bridge, wherein the boss is insertable into the socket such that the bridge resides in the circumferential opening;
the first blade interface comprises the socket and the first arm interface comprises the boss and the bridge; and
the boss is insertable into the socket along an insertion direction that is generally parallel to the access pathway.

22. The retractor system of claim 18, further comprising a guide dilator insertable into the access pathway to engage the tissue, the guide dilator comprising a first side shaped to be coupled to the first retractor blade and a second side shaped to be coupled to the second retractor blade to guide insertion of the first retractor blade and the second retractor blade into the access pathway;
wherein:
the first side comprises a first slot shaped to receive the first retractor blade;
the second side comprises a second slot shaped to receive the second retractor blade;
each of the first retractor blade and the second retractor blade comprises a groove; and
the retractor system further comprises:
a guide wire receivable in the grooves of the first retractor blade and the second retractor blade, the guide wire comprising a distal end insertable into the surgical site along the access pathway;
a first pin receivable in the grooves of the first retractor blade and the second retractor blade, the first pin comprising a first distal end anchorable in a first bone proximate the surgical site; and
a second pin receivable in the grooves of the first retractor blade and the second retractor blade, the second pin comprising a second distal end anchorable in a second bone proximate the surgical site.

\* \* \* \* \*